United States Patent [19]

Bourzat et al.

[11] Patent Number: 5,939,561
[45] Date of Patent: Aug. 17, 1999

[54] PROCESS FOR THE PREPARATION OF β-PHENYLISOSERINE AND β-LACTAM AND THEIR ANALOGUES

[75] Inventors: Jean-Dominique Bourzat, Vincennes; Alain Commercon, Vitry-Sur-Seine, both of France

[73] Assignee: Rhone-Poulence Rorer S.A., Anthony, France

[21] Appl. No.: 08/852,611

[22] Filed: May 7, 1997

Related U.S. Application Data

[62] Continuation-in-part of application No. 08/697,420, Aug. 23, 1996, Pat. No. 5,763,628, and application No. 08/537,728, filed as application No. PCT/FR94/00416, Apr. 14, 1994, abandoned, said application No. 08/697,420, is a continuation of application No. 08/295,677, filed as application No. PCT/FR93/00224, Mar. 8, 1993, Pat. No. 5,608,102.

[30] Foreign Application Priority Data

Mar. 10, 1992 [FR] France ................................. 92 02821
Apr. 16, 1993 [FR] France ................................. 93 04495

[51] Int. Cl.$^6$ .................................................. C07D 205/00
[52] U.S. Cl. .................................................. 548/953
[58] Field of Search .................................................. 548/953

[56] References Cited

U.S. PATENT DOCUMENTS

| 4,924,012 | 5/1990 | Colin et al. | 549/510 |
| 5,041,643 | 8/1991 | Tinti et al. | 562/561 |
| 5,175,315 | 12/1992 | Holton | 549/510 |
| 5,294,737 | 3/1994 | Ojima | 562/444 |
| 5,304,670 | 4/1994 | Correa et al. | 560/39 |

FOREIGN PATENT DOCUMENTS

| 0 400 971 A2 | 12/1990 | European Pat. Off. . |
| 0 402 322 A2 | 12/1990 | European Pat. Off. . |
| 0525589 A1 | 2/1993 | European Pat. Off. . |
| 91/13053 | 9/1991 | WIPO . |

OTHER PUBLICATIONS

I. Ojima et al., "Azetidines and Bisazetidines. Their Synthesis and Use as the Key Intermediates to Enantiomerically Pure Diamines, Amino Alcohols, and Polyamines", Journal of Organic Chemistry vol. 56 (1991) pp. 5263–5277.

Brieva et al., "Chemoenzymatic Syntheis of the C–13 Side Chain of Taxol: Optically–Active 3–Hydroxy–4–phenylβ–Lactam Derivatives", J. Org. Chem.; vol. 58 (1993) pp. 1068–1075.

Ojima et al., "New and Efficient Approaches to the Semi-synthesis of Taxol and its C–13 Side Chain Analogs by Means of β–Lactam Synthon Method", Tetrahedron vol. 48, (1992) pp. 6985–7012.

Chemical Abstracts, vol. 118:80677u & 80679w (1993) p. 808.

Ojima et al., "Efficient and Practical Asymmetric Synthesis of the Taxol C–13 Side Chain, N–Benzoyl–(2R, 3S)–3–phenylisoserine, and Its Analogues via Chiral 3–Hydroxy–4–aryl–β–lactams through Chiral Ester Enolate–Imine Cyclocondensation", J. Org. Chem., vol. 56 (1991) pp. 1681–1683.

Furukawa et al., A Steroselective Synthesis of α–Chloro–α–phenylacetamide by the Reaction of Optically Active Schiff Base with Dichlorocarbene, Chem. Pharm. Bull., vol. 25, (1977) pp. 181–184.

Palomo et al. "Highly Steroselective Synthesis alpha–Hydroxy beta–Amino acids through beta–Lactams: Application to the Synthesis of the Taxol and Bestatin Side Chains and Related Systems", Tetrahedron Letters, vol. 31, No. 44. pp. 6429–6432, 1990.

*Primary Examiner*—Paul J. Killos
*Attorney, Agent, or Firm*—Finnegan, Henderson, Farabow, Garrett & Dunner, L.L.P.

[57] ABSTRACT

The present invention relates to new process for the preparation of β-phenylisoserine and its analogues of general formula:

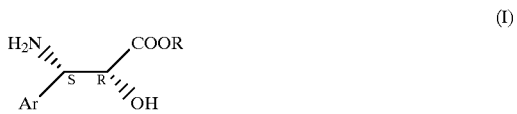

(I)

which are particularly useful for preparing taxane derivatives which have remarkable antitumour and antileukaemic activities.

6 Claims, No Drawings

PROCESS FOR THE PREPARATION OF β-PHENYLISOSERINE AND β-LACTAM AND THEIR ANALOGUES

This application is a Continuation-in-Part of application Ser. No. 08/697,420, filed Aug. 23, 1996, U.S. Pat. No. 5,763,628 which is a Continuation of application Ser. No. 08/295,677, filed Sep. 26, 1994, U.S. Pat. No. 5,608,102 Ser. No. 08/295,677 in a 371 of PCT/FR93/00224 filed Apr. 8, 1993. This application is also a Continuation-in-Part of application Ser. No. 08/537,728, filed Oct. 13, 1995, abandoned, in a 371 of PCT/FR93/00416, filed Apr. 14, 1994.

The present invention relates to new process for the preparation of β-phenylisoserine and its analogues of general formula:

$$H_2N\underset{Ar}{\overset{S\ R'}{\diagdown\diagup}}\underset{OH}{\overset{COOR}{\diagdown\diagup}} \quad (I)$$

which are particularly useful for preparing taxane derivativem which have remarkable antitumour and antileukaemic activities In the general formula (I), Ar represents an aryl radical and R represents a hydrogen atom or an alkyl radical containing 1 to 4 carbon atoms, which is optionally substituted by a phenyl radical, or a phenyl radical Preferably, Ar represents a phenyl or an α- or β-naphthyl radical which is optionally substituted by one or more atoms or radicals chosen from halogen atoms (fluorine, chlorine, bromine, iodine) and alkyl, aryl, aralkyl, alkoxy, alkylthio, aryloxy, arylthio, hydroxy, hydroxyalkyl, mercapto, formyl, acylamino, aroylamino, alkoxycarbonylemino, amino, alkylamino, dialkylamino, carboxy, alkoxycarbonyl, carbamoyl, dialkylcarbamoyl, cyano, nitro and trifluoromethyl radicals, it being understood that the alkyl radicals and the alkyl portions of the other radicals contain 1 to 4 carbon atoms and that the aryl radicals are phenyl or α- or β-naphthyl radicals.

More particularly, Ar represents a phenyl radical which is optionally substituted by one or more atoms or radicals, which are identical or different, chosen from halogen atoms and alkyl, alkoxy, amino, alkylamino, dialkylamino, acylamino, alkoxycarbonylamino and trifluoromethyl radicals.

Still more particularly, Ar represents a phenyl radical which is optionally substituted by a chlorine or fluorine atom or by an alkyl (methyl), alkoxy (methoxy), dialkylamino (dimethylamino) or acylamino (acetylamino) radical.

It is known to prepare β-phenylisoserine by hydrolysis of a lactam under the conditions described by C. Palomo et al., Tetrahedron Letters, 31, 6429–6439 (1990).

Threo-β-phenylisoserine can be obtained by the action of ammonia on a cis-β-phenylglycidic acid ester followed by the action of baryta, so as to avoid racemization on the β-phenylisoserine amide obtained as an intermediate under the conditions described by E. Kamandi et al., Arch. Pharmaj., 307 871–878 (1974).

The β-phenylisoserine can also be obtained under the conditions described in International Application PCT WO-A-91/13053 by passing via N-benzyl-β-phenylisoserine.

According to the present invention, the products of general formula (I) are obtained by hydrogenolysia of a product of general foraula:

$$Ph\overset{CH_3}{\underset{Ar}{\diagdown\diagup}}\underset{S\ R'}{\overset{NH}{\diagdown\diagup}}\underset{OH}{\overset{COOR}{\diagdown\diagup}} \quad (II)$$

in which Ar ad R are defined as above and Ph represents a phenyl radical which is optionally substituted by one or more atoms or radicals chosen from halogen (fluorine, chlorine, bromine, iodine) and alkoxy radicals containing 1 to 4 carbon atoms, alkylthio radicals containing 1 to 4 carbon atoms, amino radicals, alkylalino radicals containing 1 to 4 carbon atoms, dialkylamino radicals in which each alkyl portion contains 1 to 4 carbon atoms or nitro radicals. More particularly, Ph represents a phenyl radical which is optionally substituted by one or more radicals, which are identical or different, chosen from methoxy, methylthio, methylamino, dimethylamino or nitro radicals.

Generally, the hydrogenolysis is performed by means of hydrogen in the presence of a catalyst.

More particularly, a palladium on carbon containing 1 to 10% by weight of palladium or palladium dihydroxide on carbon containing up to 10% by weight of palladium are used as catalyst.

The hydrogenolysis is performed in an organic solvent or a mixture of organic solvents.

It is particularly advantageous to carry out the procedure in acetic acid optionally combined with an aliphatic alcohol containing 1 to 4 carbon atoms. A mixture of acetic acid and methanol is of a very special interest.

According to a preferred embodiment of the process, the procedure is carried out under a hydrogen pressure which may be between 1 and 50 bars.

The temperature for carrying out the process is generally between 20 and 80° C. and preferably between 50 and 70° C.

The hydrogen required for the hydrogenolysis may also be provided by a compound which releases hydrogen by chemical reaction or by thermal decomposition such as ammonium formate.

The product of general formula (II) may be obtained by hydrolysis or alcoholysis of a product of general formula:

$$HO\underset{O=}{\overset{R\ S}{\diagdown\diagup}}\underset{N}{\overset{Ar}{\diagdown\diagup}}\underset{CH_3}{\overset{Ph}{\diagdown}} \quad (III)$$

in which Ar and Ph are defined as above.

It is particularly advantageous to carry out an alcoholysis by means of an alcohol of general formula R—OH in which R is defined as above, the procedure being carried out in an acidic medium.

Preferably, the alcoholysis is performed by means of methanol in the presence of a strong inorganic acid such as hydrochloric acid.

It is advantageous to perform the alcoholysis at a temperature close to the reflux temperature of the reaction medium.

The product of general formula (III) may be obtained by saponification or hydrogenolysis of a product of general formula:

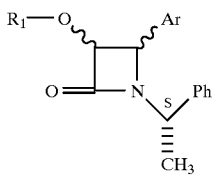
(IV)

in which Ar and Ph are defined an above and $R_1$ represents a group protecting the alcohol functional group in the form of an ester or an ether, followed by separation of the (3R,4S) diasteraoisomer of general formula (III) from the other diastereoisomers.

More particularly, $R_1$ represents an alkyl, phenylalkyl or phenyl radical or a $R'_1$—CO radical in which $R'_1$ represents an alkyl, phenylalkyl or phenyl radical.

Generally, when the alcohol functional group is protected in the form of an estar, a saponification is performed by means of an inorganic or organic base such as ammonium hydroxide, lithium hydroxide, sodium hydroxide or potassium hydroxide, in a suitable solvent.

An aqueous-organic medium such as a methanol-water or a tetrahydrofuran-water mixture is preferably used as solvent. The reaction is carried out at a temperature of between −10 and +20° C.

Generally, when the alcohol functional group is protected in the form of an ether, a hydrogenolysis is performed by means of hydrogen, optionally generated in situ, for example, by decomposition of ammonium formate, in the presence of a catalyst such as palladium black containing 1 to 10% palladium (w/w).

The separation of the (3R,4S) diasterseoisomer may be performed by selective crystallisation from a suitable organic solvent such as ethyl acetate, optionally in the presence of an aliphatic hydrocarbon such as hexane or by chromatography on silica.

The product of general formula (IV) may be obtained by cycloaddition of an imine of general formula:

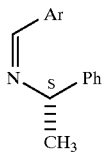
(V)

in which Ar and Ph are defined as above, onto an acid halide of general formula:

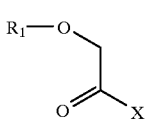
(VI)

in which $R_1$ is defined as above and X represents a halogen atom such as a bromine or chlorine atom.

Generally, the reaction is carried out at a temperature of between −20 and 50° C., preferably in the vicinity of 0° C., in the presence of a bass chosen from tertiary amines (triethylamine, N-methyl-morpholine) or pyridine, in an organic solvent chosen from optionally halogenated aliphatic hydrocarbons such as methylene chloride or chloroform and aromatic hydrocarbons such as benzene, toluene or xylenes.

The product of general formula (V) may be obtained under the conditions described by M. Furukawa et al., Chem. Pharm. Bull., 25 (1), 181–184 (1977).

The product of general formula III where Ph is substituted by $C_1$–$C_4$ alkoxy radicals, $C_1$–$C_4$ alkylthio radicals, and dialkylamino radicals in which each alkyl portion contains 1 to 4 carbon atoms, may be obtained, as described below in pages 43 et seq, by the cycloaddition of an acid halide of formula (IIIa) to a chiral imine of formula (IVa), saponifying the resulting mixture of formulae (IIa) and (IIb) products to obtain a mixture of formulae (VIa) and (VIb) products, and separating out from the formula (VIa) product.

The product of general formula (I), in which R represents a hydrogen atom, may also be obtained by saponification of a product of general formula (I), in which R represents an alkyl radical containing 1 to 4 carbon atoms, which is optionally substituted by a phenyl radical, or a phenyl radical.

Generally, the saponification is performed by means of an inorganic base such as an alkali metal hydroxide (lithium hydroxide, sodium hydroxide), an alkali metal carbonate or bicarbonate (sodium bicarbonate, potassium carbonate) in an aqueous-alcoholic medium such as a methanol-water mixture, the procedure being carried out at a temperature of between 10 and 40° C., preferably close to 25° C.

The acids of general formula (I) are particularly useful for preparing the taxane derivatives of general formula:

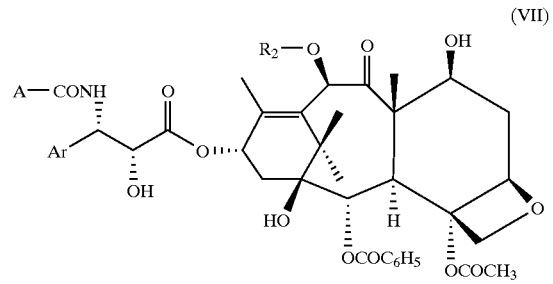
(VII)

in which Ar is defined as above, $R_2$ represents a hydrogen atom or an acetyl radical and $R_3$ represents a phenyl radical which is optionally substituted by one or more atoms or radicals, which are identical or different, chosen from halogen atoms and alkyl, hydroxyl, alkoxy, alkanoyl, alkanoyloxy, nitro, amino, alkylamino, dialkylamino, carbamoyl or trifluoromethyl radicals, the alkyl radicals and the alkyl portions of the other radicals containing 1 to 4 carbon atoms, or alternatively $R_3$ represents a radical $R_4$—O— in which $R_4$ represents:

a straight or branched alkyl radical containing 1 to 8 carbon atoms, an alkenyl radical containing 3 to 6 carbon atoms, a cycloalkyl radical containing 3 to 6 carbon atoms, a cycloalkenyl radical containing 4 to 6 carbon atoms, these radicals being optionally substituted by one or more subtituents chosen from halogen atoms and hydroxyl radicals, alkyloxy radicals containing 1 to 4 carbon atoms, dialkylamino radicals in which each alkyl portion contains 1 to 4 carbon atoms, piperidino radicals, morpholino radicals, 1-piperazinyl radicals (optionally substituted in −4 by an alkyl radical containing 1 to 4 carbon atoms or by a phenylalkyl radical whose alkyl portion contains 1 to 4 carbon atom), cycloalkyl radicals containing 4 to 6 carbon atoms, alkenyl radicals containing 4 to 6 carbon atoms, phenyl radicals, cyano radicals, carboxy radicals or alkyloxycarbonyl radicals whose alkyl portion contains 1 to 4 carbon atoms, or a phenyl radical which is optionally substituted by one or more atoms or radicals chosen from halogen atoms and alkyl radicals containing 1 to 4 carbon atoms or alkyloxy radicals containing 1 to 4 carbon atoms, or a saturated or unsaturated nitrogen-containing heterocyclyl radical containing 5 or 6 members and optionally substituted by one or more alkyl radicals containing 1 to 4 carbon atoms, which possess remarkable antitumour and antileucemic properties.

The product of general formula (VII) in which Ar represents a phenyl radical, $R_2$ represents an acetyl radical and $R_3$ represents a phenyl radical is known by the name of taxol and that for which Ar represents a phenyl radical, $R_2$ represents a hydrogen atom and $R_3$ represents a tert-butoxy radical is known by the name of Taxotere.

The taxane derivatives of general formula (VII) may be obtained by the action of an acid of general formula:

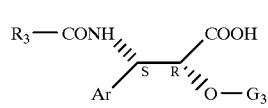
(VIII)

in which Ar and $R_3$ are defined as above and $G_3$ represents a group which protects the hydroxide functional group such as a methoxymethyl, (1-ethoxy)ethyl, benzyloxymethyl, (β-trimethylsilylethoxy)methyl, tetrahydropyranyl, 2,2,2-trichloroethoxymethyl or 2,2,2-trichloroethoxycarbonyl radical optionally in the form of a halide, an anhydride or a mixed anhydride, on a taxane derivative of general formula:

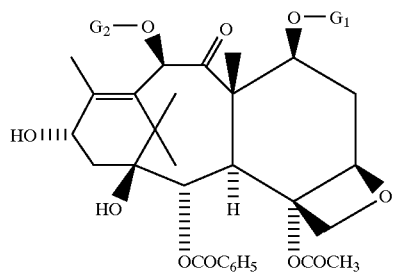
(IX)

in which $G_1$ represents a group which protects the hydroxyl functional group such an 2,2,2-trichloroethoxycarbonyl or trialkylsilyl, dialkylarylsilyl, alkyldiarylsilyl or triarylsilyl radical in which each alkyl portion contains 1 to 4 carbon atoms and each aryl portion preferably represents a phenyl radical and $G_2$ represents an acetyl radical or a group which protects the hydroxyl functional group such an a 2,2,2-trichloroethoxycarbonyl radical, to give a product of general formula:

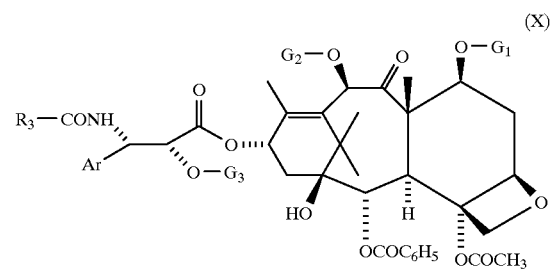
(X)

in which Ar, $R_3$, $G_1$, $G_2$ and $G_3$ are defined as above, followed by the replacement of the groups $G_1$, $G_2$ and $G_3$ by hydrogen atoms.

Generally, the esterification is performed in the presence of a condensing agent such as a carbodiimide such as dicyclohexylcarbodiimide or a reactive carbonate such as 2-pyridyl carbonate and an activating agent such as an aminopyridine such as 4-dimethylanlinopyridine or 4-pyrrolidinopyridine, the procedure being carried out in an organic solvent such as an aromatic hydrocarbon (benzene, toluene, xylene, ethylbenzene, isopropylbenzene, chlorobenzene), an other (tetrahydrofuran), a nitrile (acetonitrile) or an ester (ethyl acetate), at a temperature of between 0 and 90° C.

The replacement of the protecting groups $G_1$, $G_2$ and $G_3$ with hydrogen atoms is generally performed by treating with zinc in the presence of acetic acid at a temperature of between 30 and 60° C. or by means of an inorganic or organic acid such as hydrochloric acid or acetic acid in solution in an aliphatic alcohol containing 1 to 3 carbon atoms in the presence of zinc when one of the protecting groups represents a 2,2,2-trichloroetboxycarbonyl radical or by treating in acidic medium when one of the protecting groups represents a silylated radical.

The acid of general formula (VIII) may be obtained by saponification of an ester of general formula

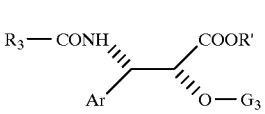
(XI)

in which Ar, $R_3$ and $G_3$ are defined as above and R' represents an alkyl radical containing 1 to 4 carbon atoms, which is optionally substituted by a phenyl radical, or a phonyl radical, by means of an inorganic base such as an alkali metal hydroxide (lithium hydroxide, sodium hydroxide), an alkali metal carbonate or bicarbonate (sodium bicarbonate, potassium carbonate) in an aqueous-alcoholic medium such as a methanol-water mixture, the procedure being carried out at a temperature of between 10 and 40° C., preferably close to 25° C.

The product of general formula (XI) may be obtained under the usual conditions for the preparation of others, and more particularly according to the processes described by J-N. Denis et al., J. Org. Chem., 51, 46–50 (1986) from the product of general formula:

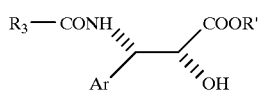    (XII)

in which Ar, $R_3$ and R' are defined as above.

The product of general formula (XII) may be obtained by the action of a benzoyl halide whose phenyl nucleus may be optionally substituted or by the action of a product of general formula:

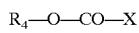    (XIII)

in which $R_4$ is defined an above and X represents a halogen atom (fluorine, chlorine) or a residue —O—$R_4$ or —O—CO—$OR_4$, on a product of general formula (I) in which R represents an alkyl radical containing 1 to 4 carbon atoms, which is optionally subatituted by a phenyl radical, or a phenyl radical.

Generally, the procedure in carried out in an organic solvent such as methylene chloride in the presence of an inorganic base such as sodium bicarbonate.

The product of general formula (XII) in which Ar represents a phenyl radical substituted by a cyano radical may be obtained by dehydration of a product of general formula (XII) in which Ar represents a phenyl radical substituted by a carbamoyl radical and the alcohol functional group is preferably protected by a silylated radical, followed by the replacement of the protecting group by a hydrogen atom.

The dehydration may be generally performed according to the usual methods for the preparation of nitriles from amidea. For example, phosphorus oxychloride in pyridine is used.

The taxane derivatives of general formula (VII) may also be obtained by first converting the product of general formula (XII) to an oxazolidine derivative of general formula

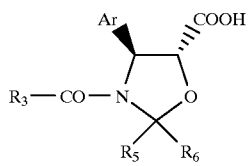    (XIV)

in which Ar and $R_3$ are defined as above and $R_5$ and $R_6$, which are identical or different, represent a hydrogen atom or an alkyl radical containing 1 to 4 carbon atoms or an aryl radical, preferably a phenyl radical optionally substituted by one or more alkoxy radicals containing 1 to 4 carbon atoms, or alternatively $R_5$ represents an alkoxy radical containing 1 to 4 carbon atoms or a trihalomethyl radical such as trichloromethyl and $R_6$ represents a hydrogen atom, or alternatively $R_5$ and $R_6$ together form with the carbon atom to which they are attached a ring having 4 to 7 members, then by esterifying the taxane derivative of general formula (IX) by means of the acid of general formula (XIV) to give a product of general formula:

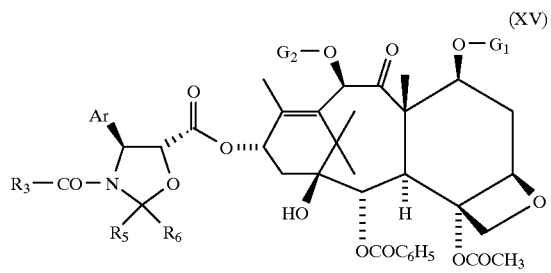    (XV)

in which Ar, $G_1$, $G_2$, $R_3$, $R_5$, and $R_6$ are defined as above, which is converted to the taxane derivative of general formula (VII) by passing, when $R_5$ and $R_6$, which are identical or different, represent an alkyl radical containing 1 to 4 carbon atoms, or an aryl radical, preferably an optionally substituted phenyl radical, or alternatively $R_5$ represents a trihalomethyl radical or a phenyl radical substituted by a trihalomethyl radical and $R_6$ represents a hydrogen atom, or alternatively $R_5$ and $R_6$ form together with the carbon atom to which they are attached a ring having 4 to 7 members, via a taxane derivative of general formula

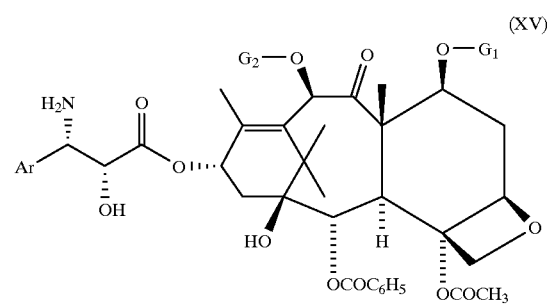    (XV)

which is acylated by means of benzoyl chloride or of a product of general formula (XIII), the procedure being carried out for example under the conditions described in PCT Application WO 9209589, before obtaining a product of general formula:

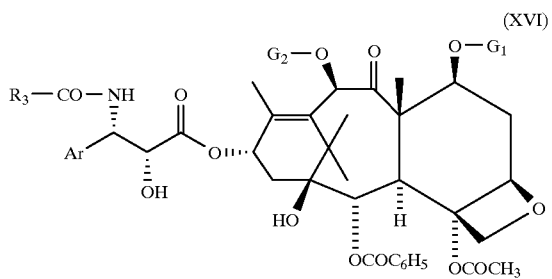    (XVI)

whose protecting groups $G_1$ and $G_2$ are replaced by hydrogen atoms under the conditions described above.

The following examples illustrate the invention.

EXAMPLE 1

To 0.91 g of a 3% dispersion of palladium on activated carbon powder, are added a solution of 1.6 g of methyl (2R,3S)-2-hydroxy-3-[(S)-1-phenyl]ethylamino-3-phenylpropionate in a mixture of 30 cm³ of methanol and 10 cm³ of acetic acid. The reaction mixture is heated to a temperature of 65° C. for 4 hours, with stirring and at a pressure of 2600 kPa (26 bars) of hydrogen, in a 250-cm$^3$ stainless steel autoclave. The reaction mixture is then cooled to a temperature close to 20° C. and filtered over sintered glass containing celite. The sintered glass is washed with 3 times 10 cm$^3$ of methanol and the filtrates are pooled and then concentrated to dryness under reduced pressure (2.7 kPa) at a temperature close to 40° C. The residue is supplemented with 40 cm$^3$ of distilled water and the solution obtained is alkalinised to a pH close to 7 by addition of 8 cm$^3$ of a 7.5N aqueous solution of sodium hydroxide and then extracted with 4 times 60 cm$^3$ of dichloromethane. The organic phases are pooled, dried over magnesium sulphate, filtered and then concentrated to dryness under reduced pressure (2.7 kPa) at 40° C. 0.74 g of white crystals are thus obtained which are recrystallised from 10 cm$^3$ of a mixture of diisopropyl ether and ethyl acetate (70–30 by volume) to give 0.54 g of methyl (2R,3S)-3-amino-2-hydroxy-3-phenylpropionate in the form of white crystals with a melting point of 101° C. and whose characteristics are as follows:

specific rotation: $[\alpha]_D^{20}=-19°$ (c=0.51; methanol)

NMR spectrum (300 MHz; CDCl$_3$) δ (ppm): 2.22 (m, 3H: –NH$_2$ and OH); 3.81 (s, 3H: —COOCH$_3$); 4.32 (s, 2H: —CHOH and —CHNH$_2$); 7.20 to 7.5 (m, 5H: —C$_6$H$_5$)

Methyl (2R,3S)-2-hydroxy-3-[(S)-1-phenyl]-ethylamino-3-phenylpropionate may be prepared in the following manner:

A solution of 0.8 g of (3R,4S)-3-hydroxy-4-phenyl-1-[(S)-1-phenyl]ethyl-2-azetidinone in a mixture of 30 cm$^3$ of methanol and 6 cm$^3$ of a 6N aqueous solution of hydrochloric acid is refluxed (65° C.) for 20 hours, then cooled to a temperature close to 20° C. and concentrated to dryness under reduced pressure (2.7 kPa) at a temperature close to 40° C. The residue is supplemented with 20 cm$^3$ of distilled water and alkalinised up to a pH close to 7 by addition of a 7.5 N aqueous solution of sodium hydroxide and then extracted with 3 times 25 cm$^3$ of dichloromethane. The organic phases are pooled, dried over magnesium sulphate, filtered and then concentrated to dryness under reduced pressure (2.7 kPa) at 40° C. 0.74 g of methyl (2R,3S)-2-hydroxy-3-[(S)-1-phenyllethylamino-3-phenylpropionate is thus obtained in the form of a pale yellow oil whose characteristics are as follows:

specific rotation: $[\alpha]_D^{20}=-22.7°$ C. (c=1.00; methanol)

NMR spectrum (200 MHz; CDCl$_3$); δ (ppm): 1.34 (d,3H, J=7 Hz: —CCH$_3$); 2.7 (m, 2H: —CNHC— and —OH); 3.71 (q, 1H, J=7 Hz: —CHNH—); 3.84 (s, 3H: —COOCH$_3$) ; 4.2 (d, 1R, J=4 Hz: —CHOH—); 4.35 (d, 1H, J=4 Hz: —CHNH—); 7.20 to 7.45 (m, 5H: —C$_6$H$_5$).

(3R,4S)-3-hydroxy-4-phenyl-1-[(S)-1-phenyl]-ethyl-2-azetidone may be prepared according to one of the following methods:

1) To a mixture of 120 cm$^3$ of a 1N aqueous solution of potassium hydroxide and 90 cm$^3$ of tetrahydrofuran, is added over 35 minutes, with stirring and at a temperature close to 0° C., a solution of 3.3 g of a mixture in a 75/25 molar ratio of the two diastereoisomers of 3-acetoxy-4-phenyl-1-[(S)-1-phenyl]ethyl-2-azetidinone, form A and form B, in 120 cm$^3$ of tetrahydrofuran. When the addition in is completed, the reaction medium is stirred at a temperature close to 0° C. for 1 hour and then supplemented with 120 cm$^3$ of a saturated aqueous solution of sodium hydrogen carbonate and 100 cm$^3$ of distilled water. The aqueous phase is separated by decantation and reextracted with 3 times 100 cm$^3$ of ethyl acetate. The organic phases are pooled, dried over magnesium sulphate, filtered and then concentrated to dryness under reduced pressure (2.7 kPa) at 40° C. 2.8 g of white crystals are thus obtained which are recrystallised from 35 cm$^3$ of a mixture of ethyl acetate and hexane (80–20 by volume) to give 1.92 g of (3R,4S)-3-hydroxy-4-phenyl-1-[(S)-1-phenyllethyl-2-azetidinone in the form of white crystals with a melting point of 162° C. and whose characteristics are an follows:

specific rotation: $[\alpha]_D^{20}=+132°$ C. (c=1.08; methanol)

NMR spectrum (200 Mz; CDCl$_3$) δ (ppm): 1.41 (d, 3H, J=7 Hz: —CHCH$_3$); 2.36 (d, 1H, J=8.5 Hz: —OH); 4.58 (d, 1H, J=4.5 Hz: —CHC$_6$H$_5$); 4.90 (dd, 1H, J=8.5 Hz and 4.5 Hz: —CHOH—); 5.06 (q, 1H, J=7 Hz: —CHCH$_3$); 7.20 to 7.50 (m, 5H —C$_6$H$_5$).

The mixture of the A form and of the B form of 3-acetoxy-4-phenyl-1-[(S)-1-phenyl]ethyl-2-azatidone may be prepared in the following manner:

To a solution of 14.63 g of (S)-N-benzylidene(1-phenylethylamine) in 180 cm$^3$ of chloroform, are added, with stirring and at a temperature close to 20° C., 19.6 cm$^3$ of triethylamine, then the reaction mixture is cooled to a temperature close to -20° C. and 5.17 cm$^3$ of 2-acetoxyacetyl chloride in 90 cm$^3$ of chloroform are added dropwise, over 75 minutes and while this temperature is maintained. The solution maintained is stirred for 16 hours at a temperature close to 20° C. and then supplemented with 300 cm$^3$ of a 2.7 N aqueous solution of hydrochloric acid. The organic phase is separated by decantation, washed with twice 300 cm$^3$ of distilled water and then with 300 cm$^3$ of a saturated aqueous solution of sodium hydrogen carbonate, dried over magnesium sulphate, filtered and then concentrated to dryness under reduced pressure (2.7 kPa) at 40° C. 16.5 g of a brown oil are thus obtained which are purified by chromatography on 800 g of silica (0.04–0.063 mm) contained in a column with a diameter of 6.8 cm [eluent:cyclohexane-ethyl acetate (70–30 by volume)], recovering 22 cm$^3$ fractions. Fractions 100 to 153 are pooled and concentrated to dryness under reduced pressure (0.27 kPa) at 40° C. 10.65 g of a mixture in a 75/25 molar ratio of the two diastercoisomers of 3-acatoxy-4-phenyl-1-[(S)-1-phenyl]-ethyl-2-azetidinone are thus obtained in the form of a yellow oil.

(S)-N-benzylidene(1-phenylethylamine) may be prepared according to the method described by M. Furukawa at al., Chem. Pharm. Bull., 1977, 25(1), 181–184.

2) By carrying out the procedure as above, but starting with 100 mg of a mixture in a 70/30 molar ratio of the two diastereoisomeres of 3-isobutyryloxy-4-phenyl-1-[(S)-1-phenyl]ethyl-2-azatidinone, form A and form B, 82 mg of (3R,4S)-3-hydroxy-4-phenyl-1-[(S)-1-phenyl]ethyl-2-azetidinone are obtained in the form of white crystals with a malting point of 162° C. whose physical characteristics are identical to those of the product obtained above.

The mixture of the A and B forms of 3-isobutyryloxy-4-phenyl-1-[(S)-1-phenyl]ethyl-2-azetidinone may be prepared by carrying out the procedure as above but starting with 1.91 g of (S)-N-benzylidene(1-phenylethylamine) and 1 g of 2-isobutyryloxyacetyl chloride. 1.27 g of a mixture in a 70/30 molar ratio of the two diastereoisomers of 3-isobutyryloxy-4-phenyl-1-[(S)-1-phenyl]ethyl-2-azetidinone are obtained in the form of a yellow oil.

2-isobutyryloxyacetyl chloride may be prepared in the following manner:

To a solution of 5 g of glycolic acid in 100 cm$^3$ of dichloromethane, maintained under an argon atmosphere, are added, with stirring and at a temperature close to 20° C., 18.3 cm$^3$ of triethylamine and then the reaction mixture is cooled to a temperature close to 5° C. and 13.8 cm$^3$ of isobutyryl chloride are added dropwise over 30 minutes while this temperature is maintained. The solution obtained is stirred for 3 hours at a temperature close to 20° C. The precipitate which appears is separated by filtration and washed with twice 10 cm³ of dichloromethane. The pooled filtrates are washed with 60 cm³ of a saturated aqueous solution of ammonium chloride, then with 30 cm³ of a saturated aqueous solution of sodium chloride, dried over magnesium sulphate, filtered and then concentrated to dryness under reduced pressure (2.7 kPa) at 40° C. 13 g of a yellow oil are thus obtained to which are added 24 cm³ of sulphinyl chloride. The solution obtained is refluxed for 2.5 hours and then distilled under reduced pressure (0.07 kPa; 0.5 mmHg). 3.4 g of 2-isobutyryloxyacetyl chloride are thus obtained in the form of a colourless liquid which distils off at 45–5° C., at a pressure of 0.07 kPa.

3) To 43 mg of a 10% dispersion of palladium on carbon powder, are added a solution of 91 mg of a mixture in a 60/40 molar ratio of the two diasteraoisomers of 3-benzyloxy-4-phenyl-1-[(S)-1-phenyl]ethyl-2-azetidinone, form A and form B, in 6 cm³ of methanol and then 32 mg of ammonium formate. The reaction mixture is maintained stirring and under an argon atmosphere for 72 hours at a temperature close to 20° C., then 56 mg of a 10% dispersion of palladium and 128 mg of ammonium formate are added. The reaction mixture is maintained stirring at this temperature for 26 hours. The reaction mixture is then filtered on sintered glass containing celite. The sintered glass is washed with 3 times 5 cm³ of dichloromethane and then the pooled filtrates are concentrated under reduced pressure (2.7 kPa) at a temperature close to 40° C. 70 mg of white crystals are thus obtained which are purified by chromatography on silica gel deposited on plates (gel 1 mm thick; 20 times 20 cm plate) in 10 mg fractions. After location under U.V. rays of the zone corresponding to the desired product, this zone is scraped and the silica is recovered and then washed on sintered glass with 10 times 5 cm³ of dichloromethane and with 5 times 2 cm³ of methanol. The filtrates are pooled and concentrated to dryness under reduced pressure (0.27 kPa) at 40° C. 28 mg of (3R,4S)-3-hydroxy-4-phenyl-1-[(S)-1-phenyl]ethyl-2-azetidinone are thus obtained in the form of white crystals with a melting point of 162° C. whose physical characteristics are identical to those of the product obtained above.

The mixture of the A and B forms of 3-benzyloxy-4-phenyl-1-[(S)-1-phenyl]ethyl-2-azetidinone may be prepared by carrying out the procedure as above but starting with 2.0 g of (S)-N-benzylidene(1-phenyl-ethylamine) and 1.38 g of 2-benzyloxyacetyl chloride. 1.25 g of a mixture in a 60/40 molar ratio of the two diastereoisomers of 3-benzyloxy-4-phenyl-1-[(S)-1-phenyl]ethyl-2-azetidinone are thus obtained in the form of a yellow oil.

EXAMPLE 2

To a solution of 0.53 g methyl (2R,3S)-3-amino-2-hydroxy-3-phenylpropionate in 8 cm³ of dichloromethane, maintained under an argon atmosphere, are added 0.25 g of sodium hydrogen carbonate and then, dropwis, at a temperature close to 20° C., a solution of 0.73 g of di-tert-butyl dicarbonate in 2 cm³ of dichloromethane. The solution obtained is stirred for 72 hours at a temperature close to 20° C. and then supplemented with 20 cm³ of distilled water. The aqueous phase is separated by decantation and then reextracted with twice 10 cm³ of dichloromethane. The organic phases are pooled, dried over magnesium sulphate, filtered and then concentrated to dryness under reduced pressure (2.7 kPa) at 40° C.

0.45 g of methyl (2R,3S)-3-tert-butoxy-carbonylamino-2-hydroxy-3-phenylpropionate are thus obtained after crystallization from disopropyl ether, in the form of white crystals with a melting point of 135° C. whose physical characteristics are identical to those described in European Patent EP 0,414,610:

specific rotation: $[\alpha]_D^{20}$=–2.6° (c=1; methanol) $[\alpha]^{20}$=–7.4° (c=1.03; chloroform)

NMR spectrum (200 MHz; CDCl₃); δ (ppm): 1.42 (s, 9H: —NHCOOC(CH₃)₃); 3.16 (d, 1H, J=5 Hz: —OH); 3.87 (s, 3H: —COOCH₃); 4.48 (m, 1H: —CHOH); 5.22 (broad d, 1H, J=10.5 Hz: —CHNHCOOC(CH₃)₃); 5.39 (d, 1H, J=10.5 Hz: —NHCOOC(CH₃)₃); 7.20 to 7.45 (m, 5H: —C₆H₅).

The product thus obtained may be converted to Taxotere under the conditions described in European Patent EP 0,336,841.

EXAMPLE 3

To 1 g of a 10% dispersion of palladium on activated carbon powder, is added a solution of 5.05 g of methyl (2R,3S)-2-hydroxy-3-[(S)-1-phenyl]ethylamino-3-(4-fluorophenyl)propionate in a mixture of 95 cm³ of methanol and 32 cm³ of acetic acid. The reaction mixture is heated at a temperature of 65° C. for 5 hours, with stirring and at a pressure of 2300 kPa (23 bars) of hydrogen, in a 1000-cm³ stainless steel autoclave. The reaction mixture is then cooled to a temperature close to 20° C. and filtered on sintered glass containing celite. The sintered glass is washed with 3 times 30 cm³ of methanol and the filtrates are pooled and then concentrated to dryness under reduced pressure (2.7 kPa) at a temperature close to 40° C.

The residue is supplemented with 50 cm³ of distilled water and the solution obtained is alkalinised to a pH close to 7 by addition of a 7.5 N aqueous solution of sodium hydroxide and then extracted with 3 times 80 cm³ of dichloromethane. The organic phases are pooled, dried over magnesium sulphate, filtered and then concentrated to dryness under reduced pressure (2.7 kPa) at 40° C. 2.45 g of methyl (2R,3S)-3-amino-2-hydroxy-3-(4-fluoro-phenyl) propionate are thus obtained in the form of cream-colored crystals with a melting point of 105° C. whose physical characteristics are as follows:

NMR spectrum: (300 MHz; CDCl₃+εCD₃COOD; δ in ppm). 3.56 (s, 3H: —COOCH₃); 4.61 and 4.69 (2 mt, 1H each: —CHOH and —CHNH₂); 7.06 [t, J=8.5 Hz, 2H: —C₆H₄F(—H3 and —H5)]; 7.46 [dd, J=8.5 and 6.5 Hz, 2H: —C₆H₄F(—H2 and —H6)].

Methyl (2R,3S)-2-hydroxy-3-[(S)-1-phenyl]-ethylamino-3-(4-fluorophenyl)propionate may be prepared in the following manner:

A solution of 5.45 g of (3R,4S)-3-hydroxy-4-(4-fluorophenyl)-1-[(S)-1-phenyl]ethyl-2-azetidinone in a mixture of 175 cm³ of methanol and 35 cm³ of a 6N aqueous solution of hydrochloric acid is refluxed (65° C.) for 18 hours, then cooled to a temperature close to 20° C. and concentrated to dryness under reduced pressure (2.7 kPa) at a temperature close to 40° C. The residue is supplemented with 150 cm³ of distilled water and alkalinised to a pH close to 7 by addition of a 7.5 N aqueous solution of sodium hydroxide and then extracted with 3 times 150 cm³ of dichloromethane. The organic phases are pooled, dried over magnesium sulphate, filtered and then concentrated to dryness under reduced pressure (2.7 kPa) at 40° C. 5.08 g of methyl (2R,3S)-2-hydroxy-3-[(S)-1-phenyl]ethylamino-3-(4-fluorophenyl)-propionate are thus obtained in the form of a pale yellow oil whose physical characteristics are an follows:

NMR spectrum: (300 MHz; CDCl$_3$; δ in ppm). 1.26 (d, J=7 Hz, 3H: —CHCH$_3$); 3.60 (q, J=7 Hz, 1H: —CHCN$_3$), 3.79 (s, 3H: —COOCH$_3$); 4.12 and 4.19 (2d, J=3 Hz, 1H each: —CHOH and —CHNH—); 7.00 [t, J=8.5 Hz, 2H: —C$_6$H$_4$F(—5 and —H5)]; 7.10 to 7.40 [mt, 7H: —C$_6$H$_5$ and —C$_6$H$_4$F(—H2 and —6)].

(3R,4S)-3-Hydroxy-4-(4-fluorophenyl)-1-[(S)-1-phenyl] ethyl-2-azetidinone may be prepared in the following manner:

To a mixture of 470 cm$^3$ of a 1 N aqueous solution of potassium hydroxide and 250 cm$^3$ of tetrahydrofuran, is added over 75 minutes, with stirring and at a temperature close to 0° C., a solution of 12.4 g of a mixture in a 75/25 molar ratio of the two diastereoisomers of 3-acatoxy-4-(4-fluorophenyl)-1-[(S)-1-phenyl]ethyl-2-azatidinone, form A and form B, in 300 cm$^3$ of tetrahydrofuran. When the addition is completed, the reaction medium is stirred at a temperature close to 0° C. for 2.5 hours and then supplemented with 250 cm$^3$ of a saturated aqueous solution of sodium hydrogen carbonate. The aqueous phase is separated by decantation and rextracted with 3 times 250 cm$^3$ of ethyl acetate. The organic phases are pooled, dried over magnesium sulphate, filtered and then concentrated to dryness under reduced pressure (2.7 kPa) at 40° C.

10.1 g of white crystals are thus obtained which are recrystallised from 55 cm$^3$ of a mixture of ethyl acetate and hexane (80–20 by volume) to give 5.45 g of (3R,4S)-3-hydroxy-4-(4-fluorophenyl)-1-[(S)-1-phenyl]ethyl-2-azetidinone in the form of white crystals with a melting point of 155° C. and whose physical characteristics are an follows:

NMR spectrum: (300 MHz; CDCl$_3$; δ in ppm). 1.29 (d, J=7.5 Hz, 3H: —CHCH$_3$); 3.59 (broad s, 1H: —OH); 4.40 (d, J=3.5 Hz, 1H: —CHC$_6$H$_4$F); 4.52 (broad d, J=3.5 Hz, 1H: —CHOH); 4.90 (q, J=7.5 Hz, 1H: —CHCH$_3$); 6.96 [t, J=8.5 Hz, 2H: —C$_6$H$_4$F(—H3 and —H5)]; 7.00 to 7.30 [mt, 7H: —C$_6$H$_5$ and —C$_6$H$_4$F (—H2 and —H6)].

The mixture of the A and B forms of 3-acetoxy-4-(4-fluorophenyl)-1-[(S)-1-phenyl]ethyl-2-azetidinone may be prepared in the following manner:

To a solution of 16.8 g of (S)-N-(4-fluoro)-benzylidene (1-phenylethylamine) in 220 cm$^3$ of chloroform, are added, with stirring and at a temperature close to 20° C., 20.8 cm$^3$ of triethylamine, then the reaction mixture is cooled to a temperature close to −20° C. and a solution of 8.2 cm$^3$ of 2-acetoxy-acetyl chloride in 80 cm$^3$ of chloroform are added dropwise, over 1 hour while this temperature is maintained. The solution obtained is stirred for 16 hours at a temperature close to 20° C. and then supplemented with 200 cm$^3$ of a 2.7 N aqueous solution of hydrochloric acid. The organic phase is separated by decantation, washed with twice 200 cm$^3$ of distilled water and then with 200 cm$^3$ of a saturated aqueous solution of sodium hydrogen carbonate, dried over magnesium sulphate, filtered and then concentrated to dryness under reduced pressure (2.7 kPa) at 40° C. 19.7 g of a brown oil are thus obtained which are purified by chromatography on 1100 g of silica (0.04–0.063 mm) contained in a column with a diameter of 8.5 cm [eluent: cyclohexane-ethyl acetate (70–30 by volume)], collecting 60-cm$^3$ fractions. The fractions containing only the desired product are pooled and concentrated to dryness under reduced pressure (0.27 kPa) at 40° C. 13.7 g of a mixture in a 75/25 molar ratio of the two diastereoisomers of 3-acetoxy-4-(4-fluorophenyl)-1-[(S)-1-phenyl]ethyl-2-azetidinone are thus obtained in the form of a yellow oil.

(S)-N-(4-Fluoro)benzylidene(1-phenylethylamine) may be prepared in the following manner:

To a solution of 12.4 g of 4-fluorobenzaldehyde in 80 cm$^3$ of dichloromethane, are added, with stirring and at a temperature close to 20° C., 13 cm$^3$ of (S)-1-phenylethylamine and 6 g of a 4 Å molecular sieve. The reaction mixture is stirred for 16 hours at a temperature close to 20° C. and then filtered on sintered glass containing celite. The sintered glass is washed with three times 20 cm$^3$ of dichloromethane and the filtrates are pooled and then concentrated to dryness under reduced pressure (2.7 kPa) at a temperature close to 40° C. 18.3 g of (S)-N-(4-fluoro) benzylidene(1-phenylethylamine) are thus obtained in the form of an opalescent oil.

EXAMPLE 4

To a solution of 2.4 g of methyl (2R,3S)-3-amino-2-hydroxy-3-(4-fluorophenyl)propionate in 60 cm$^3$ of dichloromethane, maintained under an argon atmosphere, are added 0.95 g of sodium carbonate and then, dropwise, at a temperature close to 20° C., a solution of 2.46 g of di-tert-butyl dicarbonate in 20 cm$^3$ of dichloromethane. The solution obtained is stirred for 16 hours at a temperature close to 20° C. and then supplemented with 100 cm$^3$ of distilled water. The aqueous phase is separated by decantation and then reextracted with twice 50 cm$^3$ of dichloromethane. The organic phases are pooled, dried over magnesium sulphate, filtered and then concentrated to dryness under reduced pressure (2.7 kPa) at 40° C.

2.35 g of methyl (2R,3S)-3-tert-butoxycarbonylamino-2-hydroxy-3-(4-fluorophenyl)propionate are thus obtained after recrystallisation from diisopropyl ether in the form of white crystals with a melting point of 125° C. which is converted to 4-acetoxy-2α-benzoyloxy-5β,20-epoxy-1β,7β,10β-trihydroxy-9-oxo-11-taxen-13α-yl (2R,3S)-3-tert-butoxycarbonylamino-2-hydroxy-3-(4-fluorophenyl) propionate, the procedure being carried out under the conditions described in European Patent EP 0,336,841.

EXAMPLE 5

By carrying out the procedure under the conditions described in Example 1, methyl (2R,3S)-3-amina-2-hydroxy-3-(4-trifluoromethylphenyl)propionate is prepared in the form of cream-colored crystals with a melting point of 134° C. by passing via the following intermediates:

methyl (2R,3s)-2-hydroxy-3-[(S)-1-phenyl]ethylamino-3-(4-trifluoromethylphenyl)propionate in the form of a yellow oil, (3R,4S)-3-hydroxy-4-(4-trifluoromethylphenyl)-1-[(S)-1-phenyl]ethyl-2-azetidinone in the form of white crystals with a melting point of 165° C., the mixture of the A and B forms of 3-acetoxy-4-(4-trifluoromethylphenyl)-1-[(S)-1-phenyl]ethyl-2-azetidinone in the form of a white paste, (S)-N-(4-trifluoromethyl)benzylidene(1-phenylethylamine) in the form of white crystals with a melting point below 50° C.

EXAMPLE 6

By carrying out the procedure as in Example 2, but starting with 2.73 g of methyl (2R,3S)-3-amino-2-hydroxy-3-(4-trifluoromethylphenyl)propionate, 2.43 g of methyl (2R,3S)-3-tert-butoxyearbonylamino-2-hydroxy-3-(4-trifluoromethylphenyl)propionate are obtained in the form of white crystals with a melting point of 120° C. whose physical characteristics are as follows:

NMR spectrum: (300 MHz; DMSO-d$_6$; δ in ppm). 1.40 [s, 9H: —NHCOOC(CH)$_3$]; 3.62 (s, 3H: —COOCH$_3$);

4.40 (mt, 1H: —CHOH); 5.08 [(dd, J=11 and 4.5 Hz, 1H: —CHNHCOOC(CH$_3$)$_3$]; 5.65 (d, J=6.5 Hz, 1H: —OH); 7.40 [d, J=11 Hz, 1H: —NHCOOC(CH$_3$)$_3$]; 7.59 and 7.72 (2d, J=8.5 Hz, 2H each: —C$_6$H$_4$CF$_3$(—H3, —H5 and —H2, —H6)].

The product thus obtained is converted to 4-acetoxy-2α-benzoyloxy-5β,20-epoxy-1β,7β,10β-tri-hydroxy-9-oxo-11-taxen-13α-yl (2R,3S)-3-tert-butoxycarbonyl-amino-2-hydroxy-3-(4-trifluoromethylphenyl)propionate, the procedure being carried out under the conditions described in European Patent EP 0,336,841.

EXAMPLE 7

By carrying out the procedure under the conditions described in Example 1, methyl (2R,3S)-3-amino-2-hydroxy-3-(4-dimethylaminophenyl)propionate is prepared in the form of cream-coloured crystals with a melting point of 119° C. by passing via the following intermediates methyl (2R,3S)-2-hydroxy-3-[(S)-1-phenyl]ethylamino-3-(4-dimethylaminophenyl)propionate in the form of white crystals with a melting point of 122° C., (3R,4S)-3-hydroxy-4-(4-dimethylainophenyl)-1-[(S)-1-phenyl]ethyl-2-azetidinone in the form of white crystals with a melting point of 220° C., the mixture of the A and B forms of 3-acetoxy-4-(4-dimethylaminophenyl)-1-[(S)-1-phenyl]ethyl-2-azetidinone in the form of white crystals with a melting point of 136° C., (S)-N-(4-dimethylamino)benzylidene(1-phenylethylamine) in the form of white crystals with a melting point below 50° C.

EXAMPLE 8

By carrying out the procedure as in Example 2, but starting with 0.8 g of methyl (2R,3S)-3-amino-2-hydroxy-3-(4-dimethylaminophenyl)propionate, 0.82 g of methyl (2R,3S)-3-tert-butoxycarbonylamino-2-hydroxy-3-(4-dimothylaminophenyl)propionate is obtained in the form of white crystals with a melting point of 120° C. whose physical characteristics are as follows:

NMR spectrum: (200 MHz; DMSO-d6; δ in ppm) 1.39 [s, 9H: —NHCOOC(CH$_3$)$_3$]; 2.90 [s, 6H: —N(CH$_3$)$_2$]; 3.59 (s, 3H: —COOCH$_3$); 4.21 (dd, J=7.5 and 4.5 Hz, 1H: —CHOH); 4.81 [dd, J=9.5 and 4.5 Hz, 1H: —CHNHCOOC(CH$_3$)$_3$]; 5.47 (d, J=7.5 Hz, 1H: —OH); 7.02 [d, J=9.5 Hz, 1H: —NHCOOC(CH$_3$)$_3$]; 6.66 [d, J=8.5 Hz, 2H: —C$_6$H$_4$N(CH$_3$)$_2$(—H3 and —H5)]; 7,12 (2d, J=8.5 Hz, 2H: —C$_6$H$_4$N(CH$_3$)$_2$(—H2 and —H6)].

The product thus obtained is converted to 4-acetoxy-2α-benzoyloxy-5β,20-epoxy-1β,7β,10β-trihydroxy-9-oxo-11-taxen-13α-yl (2R,3S)-3-tert-butoxycarbonylamino-2-hydroxy-3-(4-dimethylaminophenyl)propionate, the procedure being carried out under the conditions described in European Patent EP 0,336,841.

EXAMPLE 9

To 2.1 g of a 20% dispersion of palladium dihydroxide on activated carbon powder, is added a solution of 5.5 g of methyl (2R,3S)-3-(4-carbamoylphenyl)-2-hydroxy-3-[(S)-1-phenyl]-ethylaminopropionate in a mixture of 100 cm$^3$ of methanol and 3 cm$^3$ of acetic acid. The reaction mixture is maintained stirring for 60 hours at a temperature close to 20° C. and at a pressure of 120 kPa (1.2 bars) of hydrogen. The reaction mixture in then filtered on sintered glass containing celite. The sintered glass is washed with 3 times 15 cm$^3$ of methanol and the filtrates are pooled and then concentrated to dryness under reduced pressure (2.7 kPa) at a temperature close to 40° C. The crystals recovered are washed on sintered glass with 20 cm$^3$ of diethyl ether.

4.6 g of methyl (2R,3S)-3-amino-3-(4-carbamoylphenyl)-2-hydroxypropionate are thus obtained in the form of white crystals with a melting point of 206° C. and whose characteristics are as follows:

NMR spectrum: (300 MHz; DMSO-d$_6$; δ in ppm). 1.90 (s, 3H: CH$_3$COO—); 3.60 (s, 3H: —COOCH$_3$); 4.13 (limiting ab, 2H: —CHOH and —CHNH$^+$$_3$); 7.30 and 7.95 (2s, 1H each: —CONH$_3$) 7.40 [(d, J=8.5 Hz, 2H: —C$_6$H$_4$CONH$_2$(—H2 and —H6)]; 7.80 (d, J=8.5 Hz, 2H: —C$_6$H$_4$CONH$_2$(—H3 and —H5)].

Methyl (2R,3S)-3-(4-carbamoylphenyl)-2-hydroxy-3-[(S)-1-phenyl]ethylaminopropionate may be prepared in the following manner:

To a solution of 10 g of (3R,4S)-4-(4-cyanophenyl)-3-hydroxy-1-[(S)-1-phenyl]ethyl-2-azetidinone in 100 cm$^3$ of acetic acid, are added 10.9 g of mercuric acetate. The reaction medium is refluxed for 5 hours, then cooled to a temperature close to 20° C. and concentrated to dryness under reduced pressure (2.7 kPa) at a temperature close to 40° C. The residue is supplemented with 150 cm$^3$ of methanol and concentrated to dryness under reduced pressure (2.7 kPa) at a temperature close to 40° C. 300 cm$^3$ of methanol are added to the residual solid and a gaseous stream of anhydrous hydrochloric acid is injected, with stirring, into the reaction medium, at a temperature close to 40° C. for 1.5 hours. The reaction medium is concentrated to dryness under reduced pressure (2.7 kPa) at 40° C. and then poured into a mixture of 300 cm$^3$ of ethyl acetate, 300 cm$^3$ of distilled water and 100 cm$^3$ of a saturated aqueous solution of sodium hydrogen carbonate. The aqueous phase is separated by decantation and reextracted with twice 250 cm$^3$ of ethyl acetate. The organic phases are pooled, washed with twice 150 cm$^3$ of a 3% aqueous solution of sodium sulphide and then with twice 100 cm$^3$ of distilled water, dried over magnesium sulphate, filtered and then concentrated to dryness under reduced pressure (2.7 kPa) at 40° C. The crystals recovered are washed on sintered glass with 20 cm$^3$ of diethyl ether. 5.5 g of methyl (2R,3S)-3-(4-carbamoylphenyl)-2-hydroxy-3-[(S)-1-phenyl] ethylaminopropionate are thus obtained in the form of white crystals with a melting point of 130° C. whose characteristics are as follows:

NMR spectrum: (300 MHz; CDCl$_3$; δ in ppm) 1.30 (d, J=7 Hz, 3H: —CHCH$_3$); 3.65 (q, J=7 Hz, 1H: —CHCH$_3$); 3.85 (s, 3H: —COOCH$_3$); 4.25 and 4.35 (2d, J=3.5 Hz, 1H each: —CHOH— and —CHNH—); 5.97 and 6.17 (2 unresolved complexes, 1H each: —CONH$_2$); 7.20 to 7.40 (mt, 5H: —C$_6$H$_5$); 7.41 [d, J=8.5 Hz, 2H: —C$_6$H$_4$CONH$_2$(H$_2$ and H6)]; 7.81 [d, J=8.5 Hz, 2H: —C$_6$H$_4$CONH$_2$(H3 and H5)].

(3R,4S)-4-(4-Cyanophenyl)-3-hydroxy-1-[(S)-1-phenyl] ethyl-2-azetidinone may be prepared in the following manner:

Into a solution of 55.3 g of a mixture in a 65/35 molar ratio of the two diastereoisomers of 3-acetoxy-4-(4-cyanophenyl)-1-[(S)-1-phenyl]ethyl-2-azetidinone, form A and form B, in 550 cm$^3$ of methanol, is injected, with stirring, a gaseous stream of anhydrous ammonia at a temperature close to 0° C. for 3 hours. The reaction medium is concentrated to dryness under reduced pressure (2.7 kPa) at 40° C.

41 g of white crystals are obtained which are recrystallized from a mixture of 280 cm$^3$ of ethyl acetate and 70 cm$^3$ of diethyl ether. The crystals obtained are recrystallised a second time from 160 cm³ of ethyl acetate and then a third time from 100 cm³ of acetonitrile. 10 g of (3R,4S)-4-(4-cyanophenyl)-3-hydroxy-1-[(S)-1-phenyl]ethyl-2-azetidinone are thus obtained in the form of white crystals with a melting point of 139° C. and whose characteristics are as follows:

NMR spectrum: (300 MHz; CDCl₃); δ in ppm). 1.39 (d, J=7.5 Hz, 3H: —CHCH₃); 3.89 (d, J=6.5 Hz, 1N: —OH); 4.54 (d, J=4 Hz, 1H: —CHC₆H₅); 4.96 (dd, J=6.5 and 4 Hz, 1H: —CHOH); 4.96 (q, J=7.5 Hz, 1H: —CHCH₃); 7.10 to 7.40 (mt, 5H: —C₆H₅); 7.43 [d, J=8.5 Hz, 2H: —C₆H₄CN(—H2 and —H6)]; 7.66 [d, J=8.5 Hz, 2H: —C₆H₄CN(—H3 and —H5)].

The mixture of the A and B forms of 3-acetoxy-4-(4-cyanophenyl)-1-[(S)-1-phenyl]ethyl-2-azetidinone may be prepared in the following manner:

To a solution of 56.1 g of (S)-N-(4-cyano)-benzylidene (1-phenylethylamine) in 600 cm³ of chloroform, are added, with stirring and at a temperature close to 0° C., 47.6 cm³ of triethylamine and then, dropwise, over 3 hours and while this temperature is maintained, a solution of 18.6 cm³ of 2-acetoxyacetyl chloride in 500 cm³ of chloroform. The solution obtained is stirred for 16 hours at a temperature close to 20° C. and then supplemented with 250 cm³ of distilled water. The organic phase is separated by decantation, washed with 250 cm³ of distilled water, dried over magnesium sulphate, filtered and then concentrated to dryness under reduced pressure (2.7 kPa) at 40° C. 76 g of a brown oil are thus obtained which are purified by chromatography on 3500 g of silica (0.04–0.063 mm) contained in a column with a diameter of 15 cm (eluent: dichloromethane). The fractions containing only the desired product are pooled and concentrated to dryness under reduced pressure (0.27 kPa) at 40° C. 55.3 g of a mixture in a 65/35 molar ratio of the two diastereoisomers of 3-acetoxy-4-(4-cyanophenyl)-1-[(S)-1-phenyl]ethyl-2-azetidinone are thus obtained in the form of an opalescent oil.

(S)-N-(4-Cyano)benzylidene(1-phenylethylamine) may be prepared in the following manner:

To a solution of 25 g of 4-cyanobenzaldehyde in 200 cm³ of dichloromethane, are added, with stirring and at a temperature close to 20° C., 24.3 cm³ of (S)-1-phenylethylamine and 12 g of a 4 Å molecular sieve. The reaction medium is stirred for 16 hours at a temperature close to 20° C. and then filtered on sintered glass containing celite. The sintered glass is washed with 3 times 50 cm³ of dichloromethane and the filtrates are pooled and then concentrated to dryness under reduced pressure (2.7 kPa) at a temperature close to 40° C. 41.4 g of (S)-N-(4-cyano) benzylidene(1-phenylethylamine) are thus obtained in the form of a colourless oil.

EXAMPLE 10

To a solution of 2.2 g of methyl (2R,3S)-3-amino-3-(4-carbamoylphenyl)-2-hydroxypropionate in 50 cm³ of tetrahydrofuran, maintained under an argon atmosphere, are added at a temperature close to 20° C., 1.24 g of sodium hydrogen carbonate and then 1.62 g of di-tert-butyl dicarbonate. The reaction medium is stirred for 48 hours at a temperature close to 20° C. and then concentrated to dryness under reduced pressure (2.7 kPa) at 40° C. and supplemented with 20 cm³ of distilled water. The solid formed is separated by filtration, washed with 10 cm³ of distilled water and then 10 cm³ of diisopropyl ether and air dried.

2.1 g of methyl (2R,3S)-3-tert-butoxycarbonyl-amino-3-(4-carbamoylphenyl)-2-hydroxypropionate are thus obtained in the form of white crystals with a melting point of 232° C. whose physical characteristics are as follows:

NMR spectrum: (300 MHz; DMSO-d₆; δ in ppm) 1.41 [s, 9H: —NHCOOC(CH₃)₃]; 3.62 (s, 3H —COOCH₃); 4.38 (d, J=4.5 Hz, 1H: —CHOH); 5.02 [dd, J=10 and 4.5 Hz, 1H: —CHNHCOOC(CH₃)₃]; 5.65 (broad unresolved complex, 1H: —OH); 7.32 [d, J=10 Hz, 1H: —NHCOOC(CH₃)₃]; 7.39 and 8.00 (2s, 1H each: —CONH₂); 7.41 [d, J=8.5 Hz, 2H: —C₆H₄CONH₂(—H2 and —H6)]; 7.84 [d, J=8.5 Hz, 2H: —C₆H₄CONH₂ (—H3 and —H5)].

The product thus obtained in converted to 4-acatoxy-2α-benzoyloxy-5β,20-epoxy-1β,7β,10β-trihydroxy-9-oxo-11-taxen-13α-yl (2R,3S)-3-tert-butoxycarbonylamino-2-hydroxy-3-(4-carbamoylphenyl)-propionate, the procedure being carried out under the conditions described in European Patent EP 0,336,841.

EXAMPLE 11

To a mixture of 1.8 g of methyl (2R,3S)-3-tert-butoxycarbonylamino-3-(4-carbamoylphenyl)-2-hydroxypropionate and 15 cm³ of anhydrous pyridine, maintained under an argon atmosphere, are added, dropwise, at a temperature close to 20° C., 1.97 cm³ of triethylchlorosilane. When the addition is completed, the reaction medium is stirred for 3 hours at a temperature close to 20° C. and then poured into a mixture of 200 cm³ of distilled water and 50 cm³ of dichloromethane. The aqueous phase is separated by decantation and then reextracted with 3 times 50 cm³ of dichloromethane. The organic phases are pooled, dried over magnesium oulphate, filtered and then concentrated to dryness under reduced pressure (2.7 kPa) at 40° C. and the crystals recovered are washed on sintered glass with 20 cm³ of diisopropyl ether.

1.92 g of methyl (2R,3S)-3-tert-butoxycarbonylamino-3-(4-carbamoylphenyl)-2-triethyl-silyloxypropionate are thus obtained in the form of white crystals with a melting point of 165° C. whose physical characteristics are an follows:

NMR spectrum: (300 MHz; DMSO—d₆; δ in ppm). 0.43 (mt, 6H: —OSi(CH₂CH₃)₃;0.80 (t, J=7.5 Hz, 9H: —OSi(CH₂CH₃)₃;1.40 [s, 9H —NHCOOC(CH₃)₃]; 3.56 (s, 3H: —COOCH₃); 4.42 (d, J=4.5 Hz, 1H: —CHOH); 5.04 [dd, J=9.5 and 4.5 Hz, 1H: —CHNHCCOOC(CH₃)₃]; 7.33 [d, J=9.5 Hz, 1H: —NHCOOC(CH₃)₃]; 7.37 and 7.98 (2s, 1H each: —CONH₂); 7.46 [d, J=8.5 Hz, 2H: —C₆H₄CONH₂(—H2 and —H6)]; 7.84 (d, J=8.5 Hz, 2H: —C₆H₄CONH (—H3 and —H5)].

To a solution of 1.18 g of methyl (2R,3S)-3-tert-butoxycarbonylamino-3-(4-carbamoylphenyl)-2-triethylsilyloxypropionate in 20 cm³ of anhydrous pyridine, maintained under an argon atmosphere, is added, dropwise, at a temperature close to 0° C., 0.24 cm³ of phosphorus oxychloride. When the addition is completed, the reaction medium is stirred for 3 hours at a temperature close to 0° C. and then poured into a mixture of 100 cm³ of distilled water and 100 cm³ of a saturated aqueous solution of sodium hydrogen carbonate. After stirring for 5 minutes at a temperature close to 20° C., 100 cm³ of dichloromethane are added and then the aqueous phase is separated and it is reextracted with twice 80 cm³ of dichloromethane. The organic phases are pooled, dried over magnesium sulphate, filtered and then concentrated to dryness under reduced pressure (2.7 kPa) at 40° C.

The residual solid is dissolved in 30 cm³ of methanol and supplemented with 3 cm³ of a 1N aqueous solution of hydrochloric acid. The solution obtained is stirred for 45 minutes at a temperature close to 20° C. and then concentrated to dryness under reduced pressure (2.7 kPa) at 40° C. The residual solid is supplemented with 50 cm³ of a saturated aqueous solution of sodium hydrogen carbonate and then extracted with 3 times 30 cm³ of ethyl acetate. The organic phases are pooled, dried over magnesium sulphate, filtered and then concentrated to dryness under reduced pressure (2.7 kPa) at 40° C. The crystals recovered are washed on sintered glass with 20 cm³ of diisopropyl ether.

0.75 g of methyl (2R,3S)-3-tert-butoxycarbonylamino-3-(4-cyanophenyl)-2-hydroxypropionate is thus obtained in the form of white crystals with a melting point of 250° C. whose physical characteristics are as follows:

NMR spectrum: (200 MHz; DMSO-d$_6$; δ in ppm). 1.39 [s, 9H: —NHCOOC(CH$_3$)$_3$]; 3.62 (s, 3H: —COOCH$_3$); 4.39 (dd, J=8 and 4.5 Hz, 1H: —CHOH); 5.05 [dd, J=9.5 and 4.5 Hz, 1H: —CHNHCOOC(CH$_3$)$_3$]; 5.65 (d, J=8 Hz, 1H: —OH); 7.40 [d, J=9.5 Hz, 1H: —NHCOOC(CH$_3$)$_3$]; 7.53 [d, J=8.5 Hz, 2H: —C$_6$H$_4$CN(—H2 and —H6); 7.82 (d, J=8.5 Hz, 2H: —C$_6$H$_4$CN(—H3 and —H5)].

The product thus obtained is converted to 4-acetoxy-2α-benzoyloxy-5β,20-epoxy-1β,7β,10β-trihydroxy-9-oxo-11-taxen-13α-yl (2R,3S)-3-tert-butoxycarbonylamino-2-hydroxy-3-(4-cyanophenyl)-propionate, the procedure being carried out under the conditions described in European Patent EP 0,336,841.

The present invention also relates to a new process for the preparation of β-lactams of general formula:

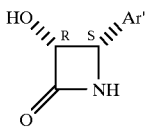

(Ia)

which are particularly useful for preparing taxoids such as taxotere or taxol.

In the general formula (Ia), Ar' represents an aryl radical.

Ar' more particularly represents a phenyl or α- or β-naphthyl radical which is optionally substituted with one or more atoms or radicals chosen from halogen atoms (fluorine, chlorine, bromine or iodine) and alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alcoxycarbonylamino, amino, alkylamino, dialkylamino, carboxyl, alkoxycarbonyl, carbamoyl, dialkylcarbamoyl, cyano, nitro and trifluoromethyl radicals, it being understood that the alkyl radicals and the alkyl portions of the other radicals contain 1 to 4 carbon atoms, that the alkenyl and alkynyl radicals contain 2 to 8 carbon atoms, and that the aryl radicals are phenyl or α- or β-naphthyl radicals, or alternatively Ar' represents a 5-membered aromatic heterocyclic radical containing one or more atoms, which may be identical or different, chosen from nitrogen, oxygen or sulphur atoms, and which is optionally substituted with one or more substituents, which may be identical or different, chosen from halogen atoms (fluorine, chlorine, bromine or iodine) and alkyl containing 1 to 4 carbon atoms, aryl containing 6 to 10 carbon atoms, alkoxy containing 1 to 4 carbon atoms, aryloxy containing 6 to 10 carbon atoms, amino, alkylamino containing 1 to 4 carbon atoms, dialkylamino in which each alkyl part contains 1 to 4 carbon atoms, acylamino in which the acyl part contains 1 to 4 carbon atoms, alkoxycarbonylamino containing 1 to 4 carbon atoms, acyl containing 1 to 4 carbon atoms, arylcarbonyl in which the aryl part contains 6 to 10 carbon atoms, cyano, carboxyl, carbamoyl, alkylcarbamoyl in which the alkyl part contains 1 to 4 carbon atoms, dialkylcarbamoyl in which each alkyl part contains 1 to 4 carbon atoms, or alkoxycarbonyl radicals in which the alkoxy part contains 1 to 4 carbon atoms.

Ar' more particularly represents a phenyl, 2- or 3-thienyl or 2- or 3-furyl radical which is optionally substituted with one or more atoms or radicals, which may be identical or different, chosen from halogen atoms and alkyl, alkoxy, amino, alkylamino, dialkylamino, acylamino, alkoxycarbonylamino and trifluoromethyl radicals.

Ar' even more particularly represents a phenyl radical which is optionally substituted with a chlorine or fluorine atom, or with an alkyl (methyl), alkoxy (methoxy), dialkylamino (dimethylamino), acylamino (acetylamino) or alkoxycarbonylamino (tert-butoxycarbonylamino) or 2- or 3-thienyl or 2- or 3-furyl radical.

European Patent Application EP 400,971 describes the preparation of a β-lactam of general formula (Ia) in which the hydroxyl function is protected, for example with a 1-ethoxyethyl radical by condensation of an acyloxyacetyl chloride with an N-benzylidene-p-methoxyaniline, followed by removal of the p-methoxyphenyl radical and replacement of the acyloxy radical by a protecting group for the hydroxyl function, such as the 1-ethoxyethyl radical. This process leads to the formation of a racemic product, for which resolution is necessary in order to obtain the 3R,4S isomer, which is useful for preparing therapeutically active taxoids.

3-Hydroxy-4-aryl-2-azetidinones of high enantiomeric purity may be obtained according to the process described by Ojima et al., J. Org. Chem., 56, 1681–1683 (1991) which uses chiral (silyloxy)acetates which are not commercially available and which require an enzymatic resolution for their preparation.

European Patent Application EP 525,589 describes the preparation of a β-lactam of general formula (Ia) in which the hydroxyl function is optionally esterified, which consists in reacting an arylimine derived from L-threonine with an acetyl halide, in separating the desired diastereoisomer and then in removing the chiral auxiliary derived from L-threonine. The imine is generally obtained in situ by reacting benzaldehyde with an L-threonine whose hydroxyl function is protected. The mixture of diastereoisomers, generally in the ratio 10/1 in favour of the 3R,4S enantiomer, is separated by the usual methods, such as crystallization or chromatography. The separation may be carried out either after formation of the azetidine ring or after removal of the protecting groups. This process requires the use of a large number of steps.

It has now been found, and this forms one aspect of the subject of the present invention, that the product of general formula (Ia) may be prepared stereoselectively by a process comprising a small number of steps from readily and economically available starting materials.

According to one aspect of the present invention, the lactams of general formula (Ia) may be prepared from a mixture of the diastereoisomers of the products of general formula:

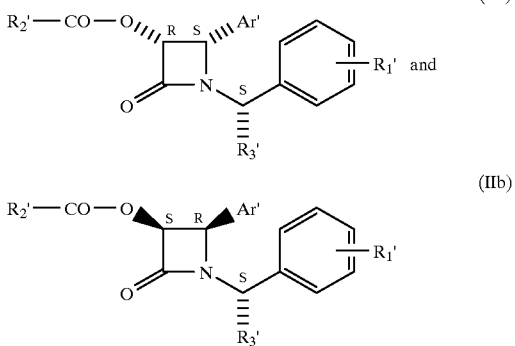

which is obtained by cycloaddition of an acid halide of general formula:

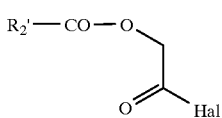

to a chiral imine of general formula:

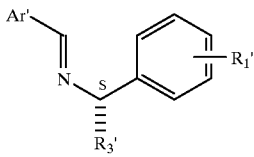

In the general formulae (IIa), (IIb), (IIIa) and (IVa),
Ar' is defined as above, R$_1$' represents one or more substituents of which one must be in the ortho or para position, which may be identical or different, chosen from alkoxy containing 1 to 4 carbon atoms such as the methoxy radical, alkylthio containing 1 to 4 carbon atoms, such as the methylthio radical, or dialkylamino radical in which each alkyl part contains 1 to 4 carbon atoms such as the dimethylamino radical, R$_2$' represents an optionally substituted alkyl radical containing 1 to 4 carbon atoms, R$_3$' represents an alkyl radical containing 1 to 4 carbon atoms, and Hal represents a halogen atom such as a chlorine or bromine atom.

According to the invention, the β-lactam of general formula (Ia) in the 3R,4S form derives from the product of general formula (IIa) after replacement of the chirality-inducing group by a hydrogen atom in order to obtain a product of general formula:

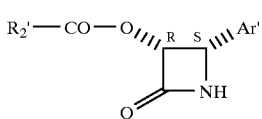

in which Ar' and R$_2$' are defined as above, which is saponified in order to obtain the product of general formula (Ia).

Replacement of the chirality-inducing group of the product of general formula (IIa) by a hydrogen atom is generally carried out by hydrolysis in the presence of ammonium cerium nitrate or 2,3-dichloro-5,6-dicyano-p-benzoquinone, or mercuric acetate, or 15 bis(trifluoroacetoxy)iodobenzene by working in water or in an aqueous-organic medium at a temperature between 0 and 50° C., preferably in the region of 20° C., or by electrochemical oxidation. A nitrile such as acetonitrile or an ester such as methyl acetate or ethyl acetate is preferably used as organic solvent.

Saponification of the ester of general formula (Va) is carried out in basic medium. Ammonia dissolved in an aliphatic alcohol such as methanol or ethanol is preferably used.

According to one implementation of the invention, replacement of the chirality-inducing group is carried out on the mixture of the products of general formulae (IIa) and (IIb) under the conditions described above, in order to obtain the mixture of the products of general formulae:

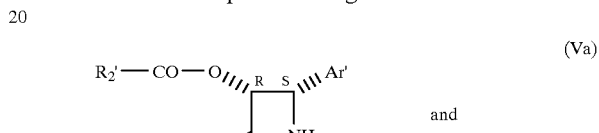

in which Ar' and R$_2$' are defined as above, which is saponified under the conditions described above in order to obtain the mixture of products of general formulae:

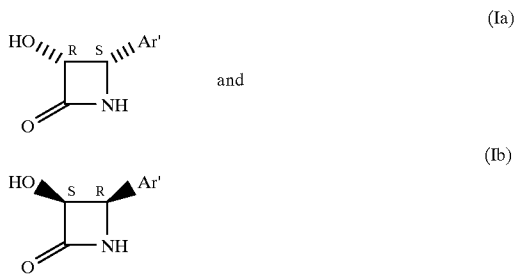

from which the product of general formula (Ia) is separated by crystallization or by chiral phase chromatography.

Separation of the products of general formula (Ia) and (Ib) is carried out by selective crystallization in a suitable organic solvent. A nitrile such as acetonitrile or an ester such as ethyl acetate is more particularly used as organic solvent.

According to another embodiment of the process according to the invention, saponification of the mixture of products of general formulae (IIa) and (IIb) is carried out in order to obtain the mixture of products of general formulae:

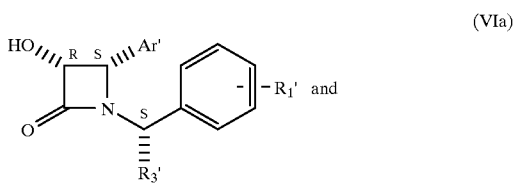

-continued

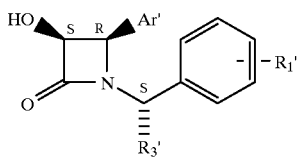

(VIb)

from which the constituent (VIa) is separated out, which is esterified in order to obtain the product of general formula (IIa), whose chirality-inducing group is replaced under the conditions described above in order to obtain the product of general formula (Va) which is saponified to the product of general formula (Ia) under the conditions described above.

Saponification of the mixture of products of general formulae (IIa) and (IIb) is carried out in basic medium. Ammonia in an aliphatic alcohol such as methanol or ethanol is preferably used.

Separation of the products of general formula (VIa) and (VIb) is carried out according to the usual methods, such as crystallization or chromatography. A selective crystallization in a suitable organic solvent such as a nitrile such as acetonitrile or an ester such as ethyl acetate is preferably carried out.

Esterification of the product of general formula (VIa) to the product of general formula (IIa) is carried out according to the usual methods by the action of an acid of general formula:

$$R_2'\text{—CO—OH} \quad (VIIa)$$

in which $R_2'$ is defined as above, or a derivative of this acid such as a halide, the anhydride or a mixed anhydride, on the product of general formula (VIa). An acid halide in the presence of a basic agent such as an inorganic base such as sodium bicarbonate or an organic base such as a tertiary amine such as triethylamine or pyridine is preferably used.

The mixture of products of general formulae (IIa) and (IIb) is obtained by the action of the product of general formula (IIIa) on the product of general formula (IVa) by generally working at a temperature between −20° C. and 50° C., preferably in the region of 0° C., in the presence of a base chosen from tertiary amines (triethylamine, N-methylmorpholine or diisopropylethylamine) or pyridine in an organic solvent chosen from optionally halogenated aliphatic hydrocarbons such as methylene chloride or chloroform and aromatic hydrocarbons such as benzene, toluene or xylenes.

The product of general formula (IVa) may be obtained under the conditions described by M. Furukawa et al., Chem. Pharm. Bull., 25, 181–184 (1977).

The products of general formula (Ia) obtained according to the process of the present invention are particularly useful for preparing taxoids such as taxotere, taxol or their analogues, for example under the conditions described in EP 400,971 or, after opening in acidic medium, according to I. Ojima et al., J. Org. Chem., 56, 1681–1683 (1991), by working under the conditions described in European Patents EP 0,336,840 and EP 0,336,841.

The examples which follow illustrate the present invention.

EXAMPLE 12

Into a solution of 1.9 g of a mixture of the two epimers of 3-acetoxy-4-phenyl-2-azetidinone, (3R,4S) form and (3S, 4R) form, in 20 cm³ of methanol is injected a stream of anhydrous ammonia gas at a temperature in the region of 20° C. for 1 hour with stirring. The reaction medium is concentrated to dryness under reduced pressure (2.7 kPa) at 40° C. The residual solid is recrystallized in 10 cm³ of ethyl acetate to give 1.2 g of white crystals whose optical rotation is: $[\alpha]^{20}_D$=+117° (c=0.52; methanol). These crystals are recrystallized three more times in acetonitrile until a constant optical rotation is obtained. 0.40 g of (3R,4S)-3-hydroxy-4-phenyl-2-azetidinone is thus obtained in the form of white crystals melting at 191° C., and for which the physical characteristics are identical in all points with those of the product described by Iwao Ojima et al., Tetrahedron, 1992, 48(34), 6985–7012.

$[\alpha]^{20}_D$=+182°(c=0.65;methanol)

N.M.R. spectrum: (200 MHz; DMSO-d₆; δ in ppm): 4.75 (d,J=5 Hz, 1H: —CHC₆H₅); 4.99 (broad t, J=5 Hz, 1H: —CHOH); 5.88 (d, J=5 Hz, 1H: —OH) ; 7.25 to 7.45 (mt, 5H: —C₆H₅); 8.52 (broad s, 1H:=NH).

The mixture of the two epimers of 3-acetoxy-4-phenyl-2-azetidinone, in the (3R,4S) form and (3S,4R) form, may be prepared in the following way:

To a solution of 5.1 g of a mixture in a 75/25 molar proportion of the two diastereoisomers of 3-acetoxy-1-[(S)-1-(4-methoxyphenyl)]ethyl-4-phenyl-2-azetidinone, in the (3R,4S) form and (3S,4R) form respectively, in 165 cm³ of acetonitrile is added, dropwise over 45 minutes and with stirring at a temperature in the region of 0° C., a solution of 27.5 g of ammonium cerium nitrate in 250 cm³ of distilled water. The solution obtained is stirred for 30 minutes at 0° C. and then for 1 hour at a temperature in the region of 20° C., and sodium hydrogen carbonate is added thereto until saturation. The reaction medium is extracted with 3 times 150 cm³ of ethyl acetate. The organic phases are combined, washed with twice 25 cm³ of distilled water, dried over magnesium sulphate, filtered and then concentrated to dryness under reduced pressure (2.7 kPa) at 40° C. 5.1 g of white crystals are obtained, which are purified by chromatography on 190 g of silica (0.063–0.2 mm) contained in a column of diameter 4 cm (eluent: dichloromethane), collecting 20 cm³ fractions. The fractions containing only the desired product are combined and concentrated to dryness under reduced pressure (2.7 kPa) at 40° C. 2.8 g of white crystals are thus obtained, which are recrystallized in 20 cm³ of ethyl acetate to give 2.2 g of a mixture of the two epimers of 3-acetoxy-4-phenyl-2-azetidinone, in the (3R,4S) form and (3S,4R) form, in the form of white crystals melting at 170° C. and for which the physical characteristics are the following.

$[\alpha]^{20}_D$=−8.2°(c=0.78;methanol)

N.M.R. spectrum: (300 MHz; CDCl₃; δ in ppm): 1.68 (s, 3H: —OCOCH₃); 5.04 (d, J=5 Hz, 1H: —CHOCOCH₃); 5.88 (dd, J=5 and 2.5 Hz, 1H: —CHC₆H₅) ; 6.63 (unres. mult., 1H: =NH) ; 7.25 to 7.45 (mt, 5H: —C₆H₅).

The mixture in a 75/25 molar proportion of the two diastereoisomers of 3-acetoxy-1-[(S)-1-(4-methoxyphenyl)] ethyl-4-phenyl-2-azetidinone, of the (3R,4S) form and (3S, 4R) form respectively, may be prepared in the following way:

To a solution of 13.2 g of (S)-N-benzylidene-[1-(4-methoxyphenyl)ethylamine] in 100 cm³ of chloroform are added, with stirring and at a temperature in the region of 20° C., 10.3 cm³ of triethylamine and the reaction mixture is then cooled to a temperature in the region of −20° C. and a solution of 4 cm³ of 2-acetoxyacetyl chloride in 50 cm³ of chloroform is added dropwise thereto over 75 minutes, while maintaining this temperature. The solution obtained is stirred for 16 hours at a temperature in the region of 20° C. and 40 cm³ of distilled water and 200 cm³ of dichloromethane are then added thereto. The organic phase is separated off after settling has taken place, washed with 20 cm³ of distilled water and then successively with 50 cm³ of 1 N aqueous hydrochloric acid solution, with 20 cm³ of distilled water, with 30 cm³ of saturated aqueous sodium hydrogen carbonate solution and with twice 10 cm³ of distilled water, dried over magnesium sulphate, filtered and then concentrated to dryness under reduced pressure (2.7 kPa) at 40° C. 16 g of a brown oil are thus obtained, which is purified by chromatography on 100 g of silica (0.063–0.2 mm) contained in a column of diameter 3 cm (eluent: dichloromethane), collecting 20 cm³ fractions. The fractions only containing the desired product are combined and concentrated to dryness under reduced pressure (2.7 kPa) at 40° C. 11.8 g of white crystals are thus obtained, which are recrystallized in 15 cm³ of diisopropyl ether to give 4.4 g of a mixture in a 75/25 molar proportion of the two diastereoisomers of 3-acetoxy-1-[(S)-1-(4-methoxyphenyl)]ethyl-4-phenyl-2-azetidinone, in the (3R,4S) form and (3S,4R) form respectively, in the form of white crystals melting at 70° C.

(S)-N-Benzylidene-[1-(4-methoxyphenyl) ethylamine] may be prepared in the following way:

To a solution of 5.6 g of benzaldehyde in 25 cm³ of dichloromethane are added, with stirring and at a temperature in the region of 20° C., 8.5 g of (S)-1-(4-methoxyphenyl) ethylamine and 5 g of 4 Å molecular sieves. The reaction mixture is stirred for 16 hours at a temperature in the region of 20° C. and then filtered through a sinter funnel containing Celite. The sinter funnel is washed 3 times with 20 cm³ of dichloromethane and the filtrates are combined and then concentrated to dryness under reduced pressure (2.7 kPa) at a temperature in the region of 40° C. 13.4 g of (S)-N-benzylidene-[1-(4-methoxyphenyl)-ethylamine] are thus obtained, in the form of a light brown oil.

$[\alpha]^{20}_D$=+13.4° (c=0.70;methanol)

(S)-1-(4-Methoxyphenyl)ethylamine may be prepared according to the method described by H. O. Bernhardt et al., Helv. Chim. Acta., 1973, 56(4), 1266–1303.

EXAMPLE 13

Into a solution of 2.0 g of (3R,4S)-3-acetoxy-4-(3-thienyl)-2-azetidinone in 100 cm³ of methanol is injected a stream of anhydrous ammonia gas at a temperature in the region of 20° C. for 1 hour with stirring. The reaction medium is concentrated to dryness under reduced pressure (2.7 kPa) at 40° C. 2.0 g of white crystals are thus obtained, which are recrystallized in 8 cm³ of ethyl acetate to give 1.3 g of (3R,4S)-3-hydroxy-4-(3-thienyl)-2-azetidinone in the form of white crystals melting at 130° C. and for which the physical characteristics are the following:

$[\alpha]^{20}_D$=+119° (c=0.64; methanol)

N.M.R. spectrum: (300 MHz; DMSO-$d_6$; δ in ppm). 4.75 [d, J=4.5 Hz, 1H: —CH—(3-thienyl)]; 4.92 (dd, J=7 and 4.5 Hz, 1H: —CHOH) ; 5.92 (d, J=7 Hz, 1H: —OH) ; 7.04 (dd, J=5 and 1.5 Hz, 1H: —H at 4 of the 3-thienyl); 7.35 (dd, J=3 and 1.5 Hz, 1H: —H at 2 of the 3-thienyl); 7.51 (dd, J=5 and 3 Hz, 1H: —H at 5 of the 3-thienyl); 8.50 (s, 1H:=NH).

(3R,4S)-3-Acetoxy-4-(3-thienyl)-2-azetidinone may be prepared in the following way:

To a solution of 5.1 g of (3R,4S)-3-acetoxy-1-[(S)-1-(4-methoxyphenyl)]ethyl-4-(3-thienyl)-2-azetidinone in 150 cm³ of acetonitrile is added, dropwise over 45 minutes and with stirring at a temperature in the region of 0° C., a solution of 27 g of ammonium cerium nitrate in 225 cm³ of distilled water. The solution obtained is stirred for 30 minutes at 0° C. and then for 1 hour at a temperature in the region of 20° C. and sodium hydrogen carbonate is added thereto until saturation. The reaction medium is extracted with 3 times 200 cm³ of ethyl acetate. The organic phases are combined, washed with 4 times 15 cm³ of distilled water, dried over magnesium sulphate, filtered and then concentrated to dryness under reduced pressure (2.7 kPa) at 40° C. 5 g of white crystals are thus obtained, which are purified by chromatography on 190 g of silica (0.063–0.2 mm) contained in a column of diameter 3.5 cm [eluent: dichloromethane/methanol (99.5/0.5 by volume)], collecting 20 cm³ fractions. The fractions containing only the desired product are combined and concentrated to dryness under reduced pressure (2.7 kPa) at 40° C. 2.1 g of (3R,4S)-3-acetoxy-4-(3-thienyl)-2-azetidinone are thus obtained in the form of white crystals melting at 168° C. and for which the physical characteristics are the following:

N.M.R. spectrum: (200 MHz; CDCl₃; δ in ppm): 1.80 (s, 3H: —OCOCH₃); 5.12 (d, J=5 Hz, 1H: —CHOCOCH₃); 5.85 [dd, J=5 and 2.5 Hz, 1H: —CH—(3-thienyl)]; 6.41 (unres. mult., 1H:=NH); 7.04 (dd, J=5 and 1 Hz, 1H: —H at 4 of the 3-thienyl); 7.27 (mt masked by the residual solvent peak: —H at 2 of the 3-thienyl); 7.35 (dd, J=5 and 3 Hz, 1H: —H at 5 of the 3-thienyl).

(3R,4S)-3-Acetoxy-1-[(S)-1-(4-methoxyphenyl)] ethyl-4-(3-thienyl)-2-azetidinone may be prepared in the following way:

To a solution of 5.1 g of (3R,4S)-3-hydroxy-1-[(S)-1-(4-methoxyphenyl)]ethyl-4-(3-thienyl)-2-azetidinone in 75 cm³ of dichloromethane are added 1.5 cm³ of pyridine, followed by dropwise addition over 15 minutes, with stirring and at a temperature in the region of 20° C., of a solution of 1.36 cm³ of acetyl chloride in 10 cm³ of dichloromethane. The solution obtained is stirred for 2.5 hours at a temperature in the region of 20° C., followed by addition of 0.75 cm³ of pyridine and 0.45 cm³ of acetyl chloride, and is maintained at a temperature in the region of 2°° C. for 1 hour with stirring. 25 cm³ of distilled water is subsequently added to the reaction mixture, stirring for 5 minutes. The aqueous phase is separated off after settling has taken place, and then extracted with 50 cm³ of dichloromethane. The organic phases are combined, washed with twice 20 cm³ of distilled water, dried over magnesium sulphate, filtered and then concentrated to dryness under reduced pressure (2.7 kPa) at 40° C. 5.9 g of a white solid are thus obtained, which solid is purified by chromatography on 110 g of silica (0.063–0.2 mm) contained in a column of diameter 3 cm [eluent: dichloromethane/methanol (99/1 by volume)], collecting 20 cm³ fractions. The fractions containing only the desired product are combined and concentrated to dryness under reduced pressure (2.7 kPa) at 40° C.

5.6 g of (3R,4S)-3-acetoxy-4-(3-thienyl)-2-azetidinone are thus obtained in the form of white crystals melting at 60° C. and for which the physical characteristics are the following:

N.M.R. spectrum: (200 MHz; CDCl₃; δ in ppm): 1.32 (d, J=7 Hz, 3H: —CHCH₃); 1.71 (s, 3H: —OCOCH₃); 3.75 (s, 3H: —OCH₃); 4.62 and 5.51 [(2d, J=5 Hz, 1H each: —CHOCOCH₃ and —CH— (3-thienyl)]; 4.87 (q, J=7 Hz, 1H: —CHCH₃); 6.73 [d, J=8.5 Hz, 2H: —C₆H₄OCH₃ (—H3 and —H5)]; 6.89 (dd, J=5 and 1.5 Hz, 1H: —H at 4 of the 3-thienyl); 7.02 [(mt, 3H: —C₆H₄OCH₃ (—H2 and H6) and —H at 2 of the 3-thienyl)]; 7.16 (dd, J=5 and 3 Hz, 1H: —H at 5 of the 3-thionyl).

(3R,4S)-3-Hydroxy-1-[(S)-1-(4-methoxyphenyl)] ethyl-4-(3-thienyl)-2-azetidinone may be prepared in the following way:

Into 10.5 g of a mixture in a 75/25 molar proportion of the two diastereoisomers of 3-acetoxy-1-[(S)-1-(4-methoxyphenyl)] ethyl-4-(3-thienyl)-2-azetidinone, in the (3R,4S) form and (3S,4R) form respectively, in 150 cm$^3$ of methanol is injected a stream of anhydrous ammonia gas at a temperature in the region of 20° C. for 2.5 hours with stirring. The reaction mixture is subsequently concentrated to dryness under reduced pressure (2.7 kPa) at 40° C. The residual solid is recrystallized a first time in 25 cm$^3$ of ethyl acetate and then a second time in 18 cm$^3$ of acetonitrile. 5.2 g of (3R,4S)-3-hydroxy-1-[(S)-1-(4-methoxyphenyl)]ethyl-4-(3-thienyl)-2-azetidinone are thus obtained in the form of white crystals melting at 150° C. and for which the characteristics are the following:

N.M.R. spectrum: (200 MHz; CDCl$_3$; δ in ppm): 1.38 (d, J=7.5 Hz, 3H: —CHCH$_3$); 3.60 (d, J=7.5 Hz, 1H: —H); 3.81 (s, 3H: —OCH$_3$); 4.63 [d, J=5 Hz, 1H: —CH— (3-thienyl)]; 4.89 (dd, J=7.5 and 5 Hz, 1H: —CHOH); 4.97 (q, J=7.5 Hz, 1H: —CHCH$_3$); 6.85 [d, J=8 Hz, 2H: —C$_6$H$_4$OCH$_3$ (—H3 and —H5)]; 7.11 (dd, J=5 and 1.5 Hz, 1H: —H at 4 of the 3-thienyl); 7.15 (d, J=8 Hz, 2H: —C$_6$H$_4$OCH$_3$ (—H2 and —H6)]; 7.22 (dd, J=3 and 1.5 Hz, 1H: —H at 2 of the 3-thienyl); 7.37 (dd, J=5 and 3 Hz, 1H: —H at 5 of the 3-thienyl).

The mixture in a 75/25 molar proportion of the two diastereoisomers of 3-acetoxy-1-[(S)-1-(4-methoxyphenyl)] ethyl-4-(3-thienyl)-2-azetidinone, in the (3R,4S) form and (3S,4R) form respectively, may be prepared in the following way:

To a solution of 9.2 g of (S)-N-(3-thienyl)-methylidene-[1-(4-methoxy)phenylethylamine] in 75 cm$^3$ of chloroform are added, with stirring and at a temperature in the region of 20° C., 10.5 cm$^3$ of triethylamine followed, after cooling the reaction mixture to a temperature in the region of −20° C., by dropwise addition of a solution of 4 cm$^3$ of 2-acetoxyacetyl chloride in 40 cm$^3$ of chloroform over 75 minutes while maintaining this temperature. The solution obtained is stirred for 16 hours at a temperature in the region of 20° C., followed by addition of 40 cm$^3$ of distilled water and 200 cm$^3$ of dichloromethane.

The organic phase is separated after settling of the phases has taken place and washed with 40 cm$^3$ of distilled water, followed successively by 75 cm 1 of 1N aqueous hydrochloric acid solution, by 25 cm$^3$ of distilled water, by 50 cm$^3$ of saturated aqueous sodium hydrogen carbonate solution and by twice 25 cm$^3$ of distilled water, dried over magnesium sulphate, filtered and then concentrated to dryness under reduced pressure (2.7 kPa) at 40° C. 16.5 g of a brown oil are thus obtained, which oil is purified by chromatography on 170 g of silica (0.063–0.2 mm) contained in a column of diameter 3.5 cm [eluent: dichloromethane/methanol (99.5/0.5 by volume)], collecting 20 cm$^3$ fractions. The fractions containing only the desired product are combined and concentrated to dryness under reduced pressure (2.7 kPa) at 40° C. 10.6 g of a mixture in a 75/25 molar proportion of the two diastereoisomers of 3-acetoxy-1-[(S)-1-(4-methoxyphenyl)]ethyl-4-(3-thienyl)-2-azetidinone, in the (3R,4S) form and (3S,4R) form respectively, are thus obtained in the form of a thick yellow oil.

(S)-N-(3-Thienyl)methylidene-[1-(4-methoxy) phenylethylamine] may be prepared in the following way:

To a solution of 3.5 g of 3-thiophonecarbaldehyde in 20 cm$^3$ of dichloromethane are added, with stirring and at a temperature in the region of 20° C., 5.8 g of (S)-1-(4-methoxyphenyl)ethylamine and 4 g of 4A molecular sieves. The reaction mixture is stirred for 16 hours at a temperature in the region of 20° C. and then filtered through a sinter funnel containing Celite. The sinter funnel is washed with 3 times 15 cm$^3$ of dichloromethane and the filtrates are combined and then concentrated to dryness under reduced pressure (2.7 kPa) at a temperature in the region of 40° C. 9.25 g of (S)-N-(3-thienyl)methylidene-[1-(4-methoxy) phenylethylaminel are thus obtained in the form of ochre-colored crystals melting at 60° C.

EXAMPLE 14

Into a solution of 3.88 g of (3R,4R)-3-acetoxy-4-(2-thienyl)-2-azetidinone in 60 cm$^3$ of methanol is injected a stream of anhydrous ammonia gas at a temperature in the region of 5° C. for one hour with stirring. The reaction mixture is concentrated to dryness under reduced pressure (2.7 kPa) at 40° C. The residual solid is purified by chromatography on 180 g of silica (0.063–0.2 mm) contained in a column of diameter 4 cm [eluent: dichloromethane/methanol (95/5 by volume)], collecting 10 cm$^3$ fractions. The fractions containing only the desired product are combined and concentrated to dryness under reduced pressure (2.7 kPa) at 40° C. 2.24 g of (3R,4R)-3-hydroxy-4-(2-thienyl)-2-azetidinone are obtained in the form of white crystals melting at 174° C. and for which the physical characteristics are the following:

$[α]^{20}_D$=+121 (c=0.53; methanol).

N.M.R. spectrum: [200 MHz; DMSO-d$_6$; δ in ppm]: 4.96 [limiting AB, 2H: —CH—(2-thienyl) and —CHOH]; 6.05 (broad unres. mult., 1H: —OH); from 6.95 to 7.10 (mt, 2H: —H at 4 and —H at 3 of the 2-thienyl); 7.47 (mt, 1H: —H at 5 of the 2-thienyl); 8.64 (unres. mult., 1H: —NH—).

(3R,4R)-3-Acetoxy-4-(2-thienyl)-2-azetidinone may be prepard in the following way:

To a solution of 3.75 g of (3R,4R)-3-acetoxy-1-[(S)-1-(3,4-dimethoxyphenyl)]ethyl-4-(2-thienyl)-2-azetidinone in 110 cm$^3$ of acetonitrile is added dropwise over 75 minutes, with stirring and at a temperature in the region of −5° C., a solution of 21.84 g of ammonium cerium nitrate in 180 cm$^3$ of saturated aqueous sodium chloride solution. At the end of the addition, 100 m$^3$ of saturated aqueous sodium hydrogen carbonate solution are added. The reaction medium is extracted with 3 times 150 cm$^3$ of ethyl acetate. The organic phases are combined, washed with 150 cm$^3$ of distilled water and then dried over magnesium sulphate, filtered and concentrated to dryness under reduced pressure (2.7 kPa) at 40° C. 4.1 g of a cream-colored meringue-like product are thus obtained, which product is purified by chromatography on 400 g of silica (0.063–0.2 mm) contained in a column of diameter 3 cm [eluent: dichloromethane/methanol (98/2 by volume)], collecting 15 cm$^3$ fractions. The fractions containing only the desired product are combined and concentrated to dryness under reduced pressure (2.7 kPa) at 40° C. 1.40 g of (3R,4R)-3-acetoxy-4-(2-thienyl)-2-azetidinone are thus obtained in the form of white crystals melting at 176° C. and for which the physical characteristics are the following:

$[α]^{20}_D$=−63 (c=0.49; methanol).

N.M.R. spectrum: [200 MHz; DMSO-d$_6$; δ in ppm]: 1.82 (s, 3H: —OCOCH$_3$); 5.28 (d, J=4.5 Hz, 1H: —CHOCOCH$_3$); 5.83 [dd, J=4.5 and 2.5 Hz, 1H: —CH—(2-thienyl)]; from 7.95 to 7.10 (mt, 2H: —H at 4 and —H at 3 of the 2-thienyl); 7.60 (broad d, J=4.5 Hz, 1H: —H at 5 of the 2-thienyl); 9.00 (unres. mult., 1H: —NH—).

(3R,4R)-3-Acetoxy-1-[(S)-1-(3,4-dimethoxyphenyl)]ethyl-4-(2-thienyl)-2-azetidinone may be prepared in the following way:

To a solution of 45.95 g of (S)-N-(2-thienyl)methylidene-[1-(3,4-dimethoxyphenyl)ethylamine] dissolved in 450 cm³ of chloroform and 70 cm³ of triethylamine is added dropwise over 3 hours, with stirring and at a temperature in the region of −30° C., a solution of 22.1 cm³ of acetoxyacetyl chloride in 150 cm³ of chloroform. On completion of the addition, the reaction medium is heated to a temperature in the region of 20° C. and maintained at this temperature for 15 hours with stirring. 200 cm³ of saturated aqueous ammonium chloride solution are subsequently added. The organic phase is separated off after settling, washed with twice 200 cm³ of distilled water and then dried over magnesium sulphate, filtered and concentrated to dryness under reduced pressure (2.7 kPa) at 40° C. 76.7 g of chestnut-brown crystals are obtained, which are recrystallized in 250 cm³ of absolute ethanol to give 25.4 g of (3R,4R)-3-acetoxy-1-(3, 4-dimethoxyphenyl)-4-(2-thienyl)-2-azetidinone in the form of white crystals melting at 100° C. and for which the physical characteristics are the following:

$[\alpha]^{20}_D = -8$ (c=0.50; methanol).

N.M.R. spectrum: [200 MHz; CDCl$_3$; δ in ppm]: 1.45 (d, J=7.5 Hz, 3H: —CHCH$_3$); 1.87 (s, 3H: —COCH$_3$); 3.82 and 3.89 (2s, 3H each: —OCH$_3$); 4.91 and 5.69 [2d, J=4.5 Hz, 1H each: —CHOCOCH$_3$ and —CH—(2-thienyl)]; 4.99 (q, J=7.5 Hz, 1H: —CHCH$_3$); from 6.70 to 7.05 [mt, 5H: —C$_6$H$_3$(OCH$_3$)$_2$ (—H2, —H5, —H6), —H at 4 and —H at 3 of the 2-thienyl]; 7.33 (dd, J=4.5 and 2 Hz, 1H: —H at 5 of the 2-thienyl).

(S)-N-(2-Thienyl)methylidene-[1-(3,4-dimethoxyphenyl) ethylamine] may be prepared in the following way:

To a solution of 43.8 g of (S)-1-(3,4-dimethoxyphenyl) ethylamine in 400 cm³ of dichloromethane are added, with stirring at a temperature in the region of 20° C., 16.8 cm³ of 2-thiophenecarboxaldehyde and 35 g of 4Å molecular sieves. The reaction mixture is stirred for 16 hours at a temperature in the region of 20° C., and then filtered through a sinter funnel containing Celite. The sinter funnel is washed with 3 times 50 cm³ of dichloromethane and the filtrates are combined and then concentrated to dryness under reduced pressure (2.7 kPa) at 40° C. 45.95 g of (S)-N-(2-thienyl)-methylidene]-[1-(3,4-dimethoxyphenyl)ethylamine are thus obtained in the form of a colourless oil for which the characteristics are the following:

$[\alpha]^{20}_D = -20$ (c=0.52; methanol).

N.M.R. spectrum: [200 MHz; CDCl$_3$; δ in ppm]: 1.58 (d, J=7 Hz, 3H: —CHCH$_3$); 3.86 and 3.90 (2s, 3H each: —OCH$_3$); 4.48 (q, J=7 Hz, 1H: —CHCH$_3$); 6.84 [d, J=8 Hz, 1H: —C$_6$H$_3$(OCB$_3$)$_2$ (—H5)]; 6.88 (dd, J=8 and 1.5 Hz, 1H: —C$_6$H$_3$(OCH$_3$)$_2$ (—H6); 6.98 (d, J=1.5 Hz, 1H: —C$_6$H$_3$(OCH$_3$)$_2$ (—H2); 7.06 (dd, J=4.5 and 3 Hz, 1H: —H at 4 of the 2-thienyl); 7.29 (broad d, J=3 Hz, 1H: —H at 3 of the 2-thienyl); 7.39 (broad d, J=4.5 Hz, 1H: —H at 5 of the 2-thienyl); 8.41 (s, 1H: —CH=N—).

(S)-1-(3,4-Dimethoxyphenyl)ethylamine may be prepared according to the method described by V. M. Potatov et al., Vestn. Mosk. Univ., Ser. 2 : Khim. 1997, 18(4), 446(CA: 88, 62047c).

EXAMPLE 15

By working as in Example 13, but using 0.8 g of (3R, 4S)-3-acetoxy-4-(4-thiazolyl)-2-azetidinone, 0.52 g of (3R, 4S)-3-hydroxy-4-(4-thiazolyl)-2-azetidinone is obtained in the form of beige-colored crystals malting at 190° C. and for which the physical characteristics are the following:

$[\alpha]^{20}_D = +112$ (c=0.51; methanol).

N.M.R. spectrum: [200 MHz; DMSO-d$_6$; δ in ppm] 4.91 [(d, J=5 Hz, 1H: —CH—(4-thiazolyl)]; 5.00 (dd, J=8 and 5 Hz, 1H: —CHOH); 5.93 (d, J=8 Hz, 1H: —OH); 7.50 (d, J=2 Hz, 1H: —H at 5 of the 4-thiazolyl); 8.55 (broad s, 1H: —NH—); 9.10 (d, J=2 Hz, 1H: —H at 2 of the 4-thiazolyl).

By working as in Example 13, using suitable starting materials, the following intermediates are prepared:

(3R,4S)-3-acetoxy-4-(4-thiazolyl)-2-azetidinone in the form 20 of white crystals melting at 155° C. and for which the physical characteristics are the following:

N.M.R. spectrum: (200 MHz; CDCl$_3$; δ in ppm): 1.85 (s, 3H: —OCOCH$_3$); 5.35 (d, J=5 Hz, 1H: —CHOCOCH$_3$); 6.03 [(dd, J=5 and 2.5 Hz, 1H: —CH—(4-thiazolyl)]; 6.45 (d, J=2.5 Hz, 1H: —NH—); 7.4 (d, J=2 Hz, 1H: —H at 5 of the 4-thiazolyl); 8.86 (d, J=2 Hz, 1H: —H at 2 of the 4-thiazolyl).

(3R,4S)-3-acetoxy-1-[(S)-1-(4-methoxyphenyl)]-ethyl-4-(4-thiazolyl)-2-azetidinone in the form of white crystals melting at 110° C. and for which the physical characteristics are the following:

N.M.R. spectrum: (300 MHz; CDCl$_3$; δ in ppm): 1.39 (d, J=7 Hz, 3H: —CHCH$_3$); 1.80 (s, 3H: —OCOCH$_3$); 3.80 (s, 3H: —OCH$_3$); 4.97 (q, J=7 Hz, 1H: —CHCH$_3$); 5.00 and 5.72 [2d, J=5 Hz, 1H each: —CHOCOCH$_3$ and —CH—(4-thiazolyl)]; 6.84 [d, J=7.5 Hz, 2H: —C$_6$H$_4$OCH$_3$ (—H3 and —H5)]; 7.13 [d, J=7.5 Hz, 2H: —C$_6$H$_4$OCH$_3$ (—H 2 and —H6)]; 7.19 (d, J=2 Hz, 1H: —H at 5 of the 4-thiazolyl); 8.79 (d, J=2 Hz, 1H: H at 2 of the 4-thiazolyl).

(3R,4S)-3-hydroxy-1-[(S)-1-(4-methoxyphenyl)]-ethyl-4-(4-thiazolyl)-2-azetidinone in the form of white crystals melting at 90° C. and for which the characteristics are the following:

N.M.R. spectrum: (200 MHz; CDCl$_3$; δ in ppm): 1.25 (d, J=7 Hz, 3H: —CHCH$_3$); 3.78 (s, 3H: —OCH$_3$); 4.53 (d, J=11 Hz, 1H: —OH); 4.65 [d, J=5 Hz, 1H: —CH—(4-thiazolyl)]; 4.93 (q, J=7 Hz, 1H: CHCH$_3$) ; 5.02 [dd, J=11 and 5 Hz, 1H: —CHOH); 6.85 [(d, J=7.5 Hz, 2H: —C$_6$H$_4$OCH$_3$ (—H3 and —H5)]; 7.13 [(d, J=7.5 Hz, 2H: —C$_6$H$_4$OCH$_3$ (—H2 and —H6)]; 7.19 (d, J=2 Hz, 1H: —H at 5 of the 4-thiazolyl); 8.85 (d, J=2 Hz, 1H: —H at 2 of the 4-thiazolyl).

the mixture in a 75/25 molar proportion of the two diastereoisomers of 3-acetoxy-1-[(S)-1-(4-methoxyphenyl)]ethyl-4-(4-thiazolyl)-2-azetidinone, in the (3R,4S) form and (3S,4R) form respectively, in the form of a thick yellow oil.

(S)-N-(4-thiazolyl)methylidene-[1-(4-methoxyphenyl) ethylamine] in the form of a thick yellow oil.

4-thiazolecarbaldehyde prepared according to the method described by A. Dondoni et al., Synthesis, 1987, 998–1001.

EXAMPLE 16

By working as in Example 13, but using 1.15 g of (3R,4S)-3-acetoxy-4-(5-thiazolyl)-2-azetidinone, 0.85 g of (3R,4R)-3-hydroxy-4-(5-thiazolyl)-2-azetidinone is obtained in the form of beige-colored crystals melting at 180° C. and for which the characteristics are the following:

[α]²⁰_D=+74 (c=0.45; methanol).

N.M.R. spectrum: [300 MHz; DMSO-d₆; δ in ppm]: 5.00 (dd, J=5 and 8 Hz, 1H: CHCH); 5.06 [dd, J=5 Hz, 1H: —CH—(5-thiazolyl)]; 6.23 (d, J=8 Hz, 1H: —CH—OH); 7.80 (broad s, 1H: —H at 4 of the 5-thiazolyl); 8.69 (mt, 1H: —NH—); 9.02 (broad s, 1H: —H at 2 of the 5-thiazolyl).

By working as in Example 13, using suitable starting materials, the following intermediates are prepared:

(3R,4R)-3-acetoxy-4-(5-thiazolyl)-2-azetidinone in the form of white crystals melting at 140° C. and for which the characteristics are the following:

N.M.R. spectrum: (300 MHz; CDCl₃; δ in ppm): 1.89 (s, 3H: —OCOCH₃); 5.36 (d, J=4.5 Hz, 1H: —CHOCOCH₃); 5.90 [(mt, 1H: —CH—(5-thiazolyl)]; 7.03 (mt, 1H: —NH—); 7.82 (s, 1H: —H at 4 of the 5-thiazolyl); 8.83 (s, 1H: —H at 2 of the 5-thiazolyl).

(3R,4R)-3-acetoxy-1-(S)-1-(4-methoxyphenyl)] ethyl-4-(5-thiazolyl)-2-azetidinone in the form of white crystals melting at 90° C. and for which the physical characteristics are the following:

N.M.R. spectrum: [300 MHz; CDCl₃; δ in ppm]: 1.38 (d, J=7 Hz, 3H: —CHCH₃); 1.90 (s, 3H: —OCOCH₃); 3.81 (s, 3H: —OCH₃); 4.97 (q, J=7 Hz, 1H: —CHCH₃); 4.97 and 5.75 [2d, J=5 Hz, 1H each: —CHOCOCH₃ and —CH—(5-thiazolyl)]; 6.85 [d, J=7.5 Hz, 2H: —C₆H₄OCH₃(—H3 and —H5)]; 7.11 (d, J=7.5 Hz, 2H: —C₆H₄OCH₃(—H2 and H6); 7.71 (s, 1H: —H at 4 of the 5-thiazolyl); 8.83 (s, 1H: —H at 2 of the 5-thiazolyl).

(3R,4R)-3-hydroxy-1-[(S)-1-(4-methoxyphenyl)] ethyl-4-(5-thiazolyl)-2-azetidinone: white crystals melting at 160 ° C. and for which the characteristics are the following:

N.M.R. spectrum: [300 MHz; CDCl₃; δ in ppm]: 1.39 (d, J=7 Hz, 3H: —CHCH₃); 3.82 (s, 3H: —OCH₃) ; 4.85 and 5.00 [2d, J=5 Hz, 1H each: —CH—(5-thiazolyl) and —CHOH]; 4.95 (q, J=7 Hz, 1H: CHCH₃); 5.18 (broad s, 1H: —OH); 6.86 [d, J=7.5 Hz, 2H: C₆H₄OCH₃(—H3 and —H5)]; 7.15 (d, J=7.5 Hz, 2H: —C₆H₄OCH₃(—H2 and —H6)]; 7.68 (s, 1H: —H at 4 of the 5-thiazolyl); 8.82 (s, 1H: —H at 2 of the 5-thiazolyl).

the mixture in a 75/25 molar proportion of the two diastereoisomers of 3-acetoxy-1-[(S)-1-(4-methoxyphenyl)]ethyl-4-(5-thiazolyl)-2-azetidinone, in the (3R,4R) form and (3S,4S) form respectively, in the form of a thick yellow oil.

(S)-N-(5-thiazolyl)methylidene-[1-(4-methoxy)phenyl-ethylamine] in the form of a thick yellow oil.

5-thiazolecarboxaldehyde prepared according to the method described by A. Dondoni et al., Synthesis, 1987, 998–1001.

All of the above refernces are hereby expressly incorporated by refence in their entirety.

We claim:

1. Process for the preparation of a β-lactam of general formula:

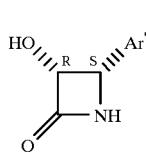

(Ia)

in which Ar' represents a phenyl or α- or β-naphthyl radical which is optionally substituted with one or more atoms or radicals chosen from halogen atoms (fluorine, chlorine, bromine or iodine) and alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alcoxycarbonylamino, amino, alkylamino, dialkylamino, carboxyl, alkoxycarbonyl, carbamoyl, dialkylcarbamoyl, cyano, nitro and trifluoromethyl radicals, it being understood that the alkyl radicals and the alkyl portions of the other radicals contain 1 to 4 carbon atoms, that the alkenyl and alkynyl radicals contain 2 to 8 carbon atoms and that the aryl radicals are phenyl or α- or β-naphthyl radicals, or alternatively Ar' represents a 5-membered aromatic heterocyclic radical containing one or more atoms, which may be identical or different, chosen from nitrogen, oxygen or sulphur atoms, and which is optionally substituted with one or more substituents, which may be identical or different, chosen from halogen atoms (fluorine, chlorine, bromine or iodine) and alkyl containing 1 to 4 carbon atoms, aryl containing 6 to 10 carbon atoms, alkoxy containing 1 to 4 carbon atoms, aryloxy containing 6 to 10 carbon atoms, amino, alkylamino containing 1 to 4 carbon atoms, dialkylamino in which each alkyl part contains 1 to 4 carbon atoms, acylamino in which the acyl part contains 1 to 4 carbon atoms, alkoxycarbonylamino containing 1 to 4 carbon atoms, acyl containing 1 to 4 carbon atoms, arylcarbonyl in which the aryl part contains 6 to 10 carbon atoms, cyano, carboxyl, carbamoyl, alkylcarbamoyl in which the alkyl part contains 1 to 4 carbon atoms, dialkylcarbamoyl in which each alkyl part contains 1 to 4 carbon atoms, or alkoxycarbonyl radicals in which the alkoxy part contains 1 to 4 carbon atoms, characterized in that the chirality-inducing group of a product of general formula:

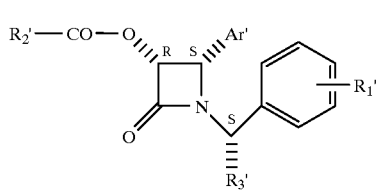

(IIa)

or of a mixture of products of general formula:

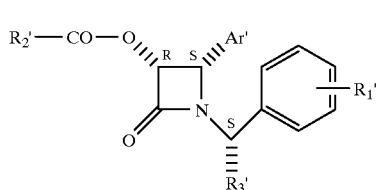

(IIa)

and

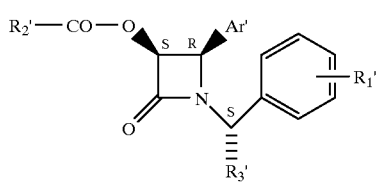 (IIb)

in which $R_1'$ represents one or more substituents of which one must be in the ortho or para position, which are identical or different, and which are chosen from alkoxy containing 1 to 4 carbon atoms, alkylthio in which the alkyl part contains 1 to 4 carbon atoms or dialkylamino radical in which each alkyl part contains 1 to 4 carbon atoms, $R_2'$ represents an alkyl radical containing 1 to 4 carbon atoms and $R_3'$ represents an alkyl radical containing 1 to 4 carbon atoms, is replaced in order to obtain the product of general formula:

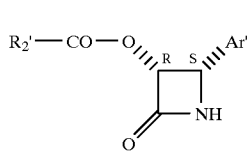 (Va)

or a mixture of products of general formula:

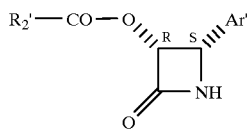 (Va)

and

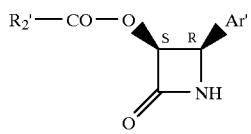 (Vb)

in which Ar' and $R_2'$ are defined as above, which product is saponified in order to obtain the product of general formula:

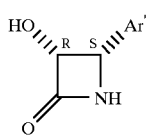 (Ia)

or a mixture of products of general formula:

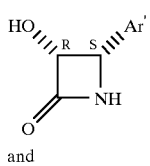 (Ia)

and

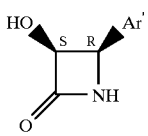 (Ib)

from which the product of general formula (Ia) is separated out by selective crystallization or by chiral phase chromatography.

2. Process according to claim 1, characterized in that replacement of the chirality-inducing group is carried out by hydrolysis in the presence of ammonium cerium nitrate or 2,3-dichloro-5,6-dicyano-p-benzoquinone or mercuric acetate or bis(trifluoroacetoxy)iodobenzene, by working in water or in an aqueous-organic medium at a temperature between 0 and 50° C., or by electrochemical oxydation.

3. Process according to claim 2, characterized in that the solvent is chosen from nitriles and esters.

4. Process according to claim 1, characterized in that the saponification is carried out using ammonia dissolved in an aliphatic alcohol.

5. Process according to claim 1, characterized in that saponification of the mixture of products of general formula:

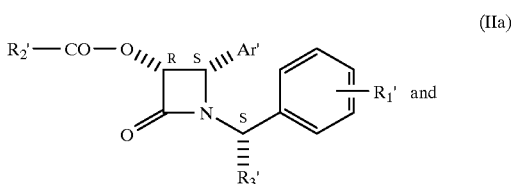 (IIa)

and

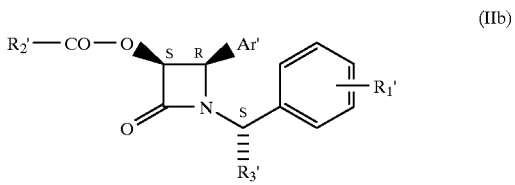 (IIb)

in which Ar', $R_1'$, $R_2'$ and $R_3'$ are defined as above, is carried out in order to obtain a mixture of products of general formulae:

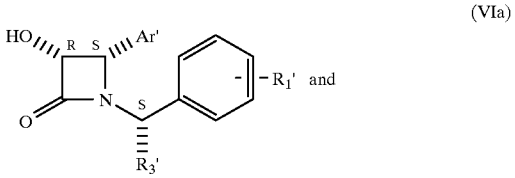 (VIa)

and

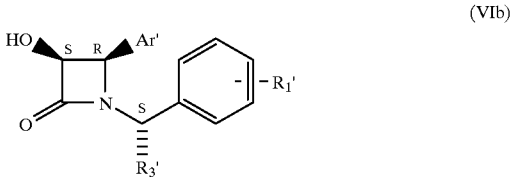 (VIb)

in which Ar', $R_1'$ and $R_3'$ are defined as above, from which the constituent of general formula (VIa) is separated out, which is esterified using an acid of general formula:

$R_2'$—CO—OH (VIIa)

in which $R_2'$ is defined as above, in order to obtain the product of general formula:

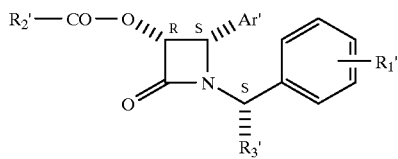

(IIa)

in which Ar', $R_1'$, $R_2'$ and $R_3'$ are defined as above, from which the chirality-inducing group is replaced in order to obtain the product of general formula:

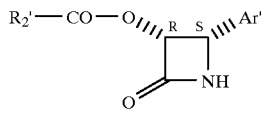

(Va)

which is saponified in order to obtain the product of general formula (Ia).

6. Process according to claim 1, characterized in that the product of general formula (IIa) or the mixture of products of general formula (IIa) and (IIb) is obtained by the action of an acid halide of general formula:

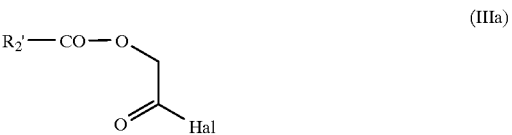

(IIIa)

in which $R_2'$ is defined as in claim 1 and Hal represents a halogen atom, on a chiral imine of general formula:

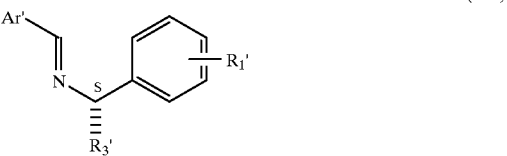

(IVa)

in which Ar', $R_1'$ and $R_3'$ are defined as in claim 1.

* * * * *